US006955884B2

(12) United States Patent
Lund et al.

(10) Patent No.: US 6,955,884 B2
(45) Date of Patent: Oct. 18, 2005

(54) METHODS FOR IDENTIFYING COMPOUNDS THAT INHIBIT CD38 ACTIVITY

(75) Inventors: Frances E. Lund, Saranac Lake, NY (US); Troy D. Randall, Saranac Lake, NY (US); Santiago Partida-Sánchez, Saranac Lake, NY (US)

(73) Assignee: Trudeau Institute, Inc., Saranac Lake, NY (US)

( * ) Notice: Subject to any disclaimer, the term of this patent is extended or adjusted under 35 U.S.C. 154(b) by 197 days.

(21) Appl. No.: 09/982,616

(22) Filed: Oct. 17, 2001

(65) Prior Publication Data

US 2002/0127646 A1 Sep. 12, 2002

Related U.S. Application Data

(60) Provisional application No. 60/241,065, filed on Oct. 17, 2000.

(51) Int. Cl.[7] .......................... G01N 33/53; C12N 5/00; C12N 5/02
(52) U.S. Cl. ........................................ 435/7.1; 435/375
(58) Field of Search .................................. 435/7.1, 375

(56) References Cited

U.S. PATENT DOCUMENTS

5,958,723 A  9/1999  Abramovitz et al. ....... 435/69.1

OTHER PUBLICATIONS

Graeff R, Munshi C, Aarhus R, Johns M, Lee HC. A single residue at the active site of CD38 determines its NAD cyclizing and hydrolyzing activities. J. Biol. Chem. 2001;276:12169–12173.
Day TA, Haithcock J, Kimber M, Maule AG. Functional ryanodine receptor channels in flatworm muscle fibres. Parasitology 2000;120:417–422.
Munshi C, Aarhus R, Graeff R, Walseth TF, Levitt D, Lee HC. Identification of the enzymatic active site of CD38 by site–directed mutagenesis. J. Biol. Chem. 2000;275:21566–21571.
Guse AH. Cyclic ADP–ribose: a novel $Ca^{2+}$ mobilising second messenger. Cell. Signal 1999;11:309–316.
Guse AH, da Silva CP, Berg I, Skapenko AL, Weber K, Heyer P, Hohenegger M, Ashamu GA, Schulze–Koops H, Potter BV, Mayr GW. Regulation of calcium signalling in T lymphocytes by the second messenger cyclic ADP–ribose. Nature 1999;398:70–73.
Lee HC. A unified mechanism of enzymatic synthesis of two calcium messengers: cyclic ADP–ribose and NAADP. Biol. Chem. 1999;380:785–793.
Lund FE, Muller–Steffner HM, Yu N, Stout CD, Schuber F, Howard MC. CD38 signaling in B lymphocytes is controlled by its ectodomain but occurs independently of enzymatically generated ADP–ribose or cyclic ADP–ribose. J. Immunol. 1999;162:2693–2702.
Munshi C, Thiel DJ, Mathews II, Aarhus R, Walseth TF, Lee HC. Characterization of the active site of ADP–bibosyl cyclase. J. Biol Chem 1999;274:30770–30777.
Berthelier V, Tixier JM, Muller–Steffner H, Schuber F, Deterre P. Human CD38 is an authentic NAD(P)+ glycohydrolase. Biochem. J 1998;330:1383–1390.
Cockayne DA, Muchamuel T, Grimaldi JC, Muller–Steffner H, Randall TD, Lund FE, Murray R, Schuber F, Howard MC. Mice deficient for the ecto–nicotinamide adenine dinucleotide glycohydrolase CD38 exhibit altered humoral immune responses. Blood 1998;92:1324–1333.
Fernandez JE, Deaglio S, Donati D, Beusan IS, Corno F, Aranega A, Forni M, Falini B, Malavasi F. Analysis of the distribution of human CD38 and of its ligand CD31 in normal tissues. : J. Biol. Regul. Homeost. Agents 1998;12:81–91.
Silva CL, Cunha VM, Mendonca–Silva DL, Noel F. Evidence of ryanodine receptors in schistosoma mansoni. Biochem. Pharmacol. 1998;56:997–1003.
Graeff RM, Walseth TR, Lee HC. Radioimmunoassay for measuring endogenous levels of cyclic ADP–ribose in tissues. Methods Enzymol. 1997;280:230–241.
Higashida H, Yokoyama S, Hashii M, Taketo M, Higashida M, Takayasu T, Ohshima T, Takasawa S, Okamoto H, Noda M. Muscarinic receptor–mediated dual regulation of ADP–ribosyl cyclase in NG108–15 neuronal cell membranes. J. Biol. Chem. 1997;272:31277–31277.
Vu CQ, Coyle DL, Jacobson MK. Natural occurrence of 2'–phospho–cyclic ADP ribose in mammalian tissues. Biochem. Biophys. Res. Commun. Jul. 30, 1997;236(3):723–726.
Vu CQ, Coyle DL, Tai HH, Jacobson EL, Jacobson MK. Intramolecular ADP–ribose transfer reactions and calcium signalling. Potential role of 2'–phospho–cyclic ADP–ribose in oxidative stress. Adv. Exp. Med. Biol. 1997;419:381–388.

(Continued)

Primary Examiner—Christina Chan
Assistant Examiner—Michail A Belyavskyi
(74) Attorney, Agent, or Firm—Kenyon & Kenyon

(57) ABSTRACT

The present invention relates to methods for modulating the migratory activity of cells expressing CD38 for the treatment of disorders including, but not limited to, inflammation, ischemia, asthma, autoimmune disease, diabetes, arthritis, allergies, infection with pathogenic organisms and transplant rejection. Such cells include, for example, neutrophils, lymphocytes, eosinophils, macrophages and dentritic cells. The invention further relates to drug screening assays designed to identify compounds that modulate the ADP-ribosyl cyclase activity of CD38 and the use of such compounds in the treatment of disorders involving CD38 modulated cell migration. The invention is based on the discovery that CD38 ADP-ribosyl cyclase activity is required for chemotaxis. Furthermore, the invention relates to methods for identifying compounds that modulate the enzyme activity of the *S. mansoni* CD38 homologue and using those compounds in the treatment of pathologic disorders caused by helminth infection. This is based on the discovery that helminths such as *S. mansoni* express CD38 homologues.

5 Claims, 19 Drawing Sheets

OTHER PUBLICATIONS

Figure 1:
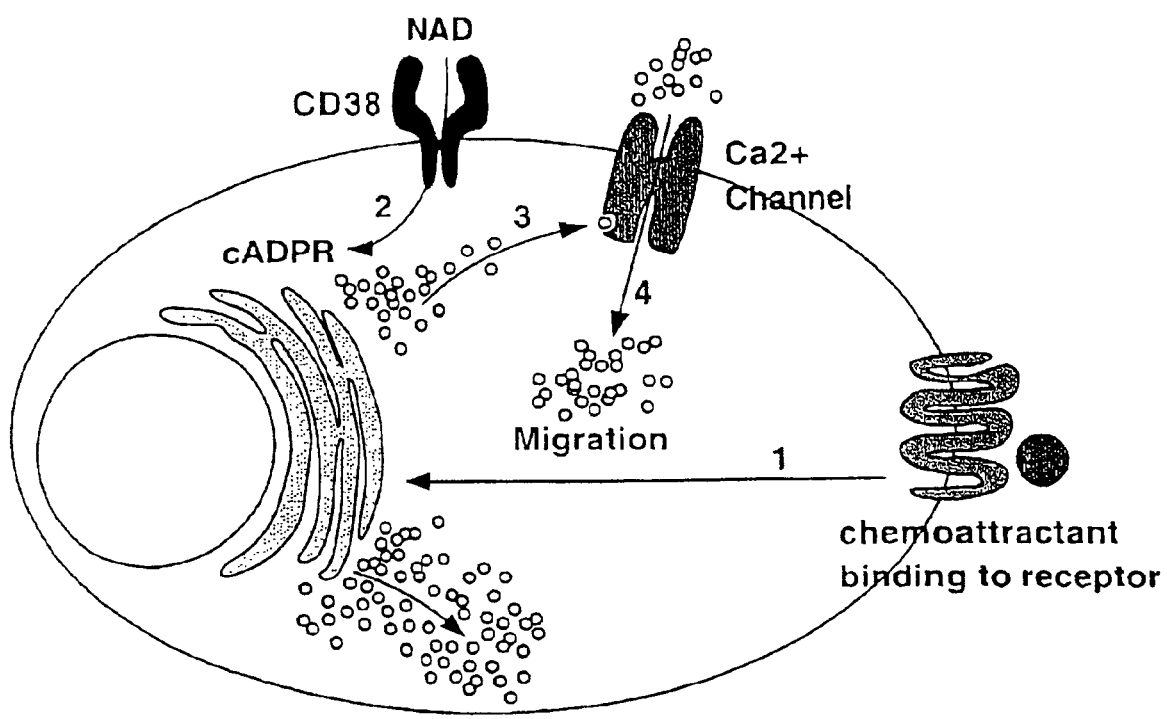

Graeff RM, Walseth TF, Hill HK, Lee HC. Fluorescent analogs of cyclic ADP–ribose: synthesis, spectral characterization, and use. Biochemistry 1996;35:379–386.

Muller–Steffner HM, Augustin A, Schuber F. Mechanism of cyclization of pyridine nucleotides by bovine spleen NAD+ glycohydrolase. Mechanism of cyclization of pyridine nucleotides by bovine spleen NAD+ glycohydrolase. J. Biol. Chem. 1996;271:23967–23972.

Prasad GS, McRee DE, Stura EA, Levitt DG, Lee HC, Stout CD. Crystal structure of Aplysia ADP ribosyl cyclase, a homologue of the bifunctional ectozyme CD38. Nat. Struct. Biol. 1996;3:957–964.

Gadangi P, Longaker M, Naime D, Levin RI, Recht PA, Montesinos MC, Buckley MT, Carlin G, Cronstein BN. The anti–inflammatory mechanism of sulfasalazine is related to adenosine release at inflamed sites. J. Immunol. 1996:156:1937–1941.

Aarhus R, Graeff RM, Dickey DM, Walseth TF, Lee HC. ADP–ribosyl cyclase and CD38 catalyze the synthesis of a calcium–mobilizing metabolite from NADP. J. Biol. Chem. 1995;270:30327–30333.

Takashi K, Kukimoto I, Tokita K, Inageda K, Inoue S, Kontani K, Hoshino S, Nishina H, Kanaho Y, Katada T. Accumulation of cyclic ADP–ribose measured by a specific radioimmunoassay in differentiated human leukemic HL–60 cells with all–trans–retinoic acid. FEBS Lett. 1995;371:204–208.

Bronstein I, Fortin JJ, Voyta JC, Juo RR, Edwards B, Olesen CE, Lijam N, Kricka LJ. Chemiluminescent reporter gene assays: sensitive detection of the GUS and SEAP gene products. Biotechniques 1994;17:172–174, 176–177.

Day TA, Bennett JL, Pax RA. Serotonin and its requirement for maintenance of contractility in muscle fibres isolated from *Schistosoma mansoni*. Parasitology 1994;108:425–432.

Day TA, Maule AG, Shaw C, Halton DW, Moore S, Bennett JL, Pax RA. Platyhelminth FMRFamide–related peptides (FaRPs) contract *Schistosoma mansoni* (Trematoda: Digenea) muscle fibres in vitro. Parasitology 1994;109:455–459.

Graeff RM, Walseth TF, Fryxell K, Branton WD, Lee HC. Enzymatic synthesis and characterization of cyclic GDP–ribose. A procedure for distinguishing enzymes with ADP–ribosyl cyclase activity. J. Biol. Chem. 1994;269:30260–30267.

Koguma T, Takasawa S, Tohgo A, Karasawa T, Furuya Y, Yonekura H, Okamoto H. Cloning and characterization of cDNA encoding rat ADP–ribosyl cyclase/cyclic ADP–ribose hydrolase (homologue to human CD38) from islets of Langerhans. Biochim. Biophys. Acta 1994;1223:160–162.

Murphy PM. The molecular biology of leukocyte chemoattractant receptors. Annu. Rev. Immunol. 1994;12:593–633.

Weis JH. 'Race no more': an alternative approach to cloning the 5' end of transcripts. Nucleic Acids Res. 1994;22:3427–3428.

Day TA, Orr N, Bennett JL, Pax RA. Voltage–gated currents in muscle cells of *Schistosoma mansoni*. Parasitology 1993;106:471–477.

Galione A, White A, Willmott N, Turner M, Potter BV, Watson SP. cGMP mobilizes intracellular Ca2+ in sea urchin eggs by stimulating cyclic ADP–ribose synthesis. Nature 1993;365:456–459.

Harada N, Santos–Argumedo L, Chang R, Grimaldi JC, Lund FE, Brannan CI, Copeland NG, Jenkins NA, Heath AW, Parkhouse RM, Howeard M. Expression cloning of a cDNA encoding a novel murine B cell activation marker. Homology to human CD38. J. Immunol. 1993;151:3111–3118.

Howard M, Grimaldi JC, Bazan JF, Lund FE, Santos–Argumedo L, Parkhouse RM, Walseth TF, Lee HC. Formation and hydrolysis of cyclic ADP–ribose catalyzed by lymphocyte antigen CD38. Science 1993;262:1056–1059.

Sorrentino V, Volpe P. Ryanodine receptors: how many, where and why? Trends Pharmacol. Sci. 1993;14:98–103.

Hakamato Y, Nakai J, Takeshima H, Imoto K. Primary structure and distribution of a novel ryanodine receptor/calcium release channel from rabbit brain. FEBS Lett 1992;312:229–235.

Shinkai Y, Rathbun G, Lam KP, Oltz EM, Stewart V, Mendelsohn M, Charron J, Datta M, Young F, Stall AM, Alt FW. RAG–2–deficient mice lack mature lymphocytes owing to inability to initiate V(D)J rearrangement. Cell 1992;68:855–867.

Galione A, Lee HC, Busa WB. Ca(2+)–induced Ca2+ release in sea urchin egg homogenates: modulation by cyclic ADP–ribose. Science 1991;253:1143–1146.

Lee HC, Aarhus R. ADP–ribosyl cyclase: an enzyme that cyclizes NAD+ into a calcium–mobilizing metabolite. Cell Regul. 1991;2:203–209.

Jackson DG, Bell JI. Isolation of a cDNA encoding the human CD38 (T10) molecule, a cell surface glycoprotein with an unusual discontinuous pattern of expression during lymphocyte differentiation. J. Immunol. 1990;144:2811–2815.

Baggiolini M, Walz A, Kunkel SL. Neutrophil–activating peptide–1/interleukin 8, a novel cytokine that activates neutrophils. J. Clin. Invest. 1989;84:1045–1049.

Lee HC, Walseth TF, Bratt GT, Hayes RN, Clapper DL. Structural determination of a cyclic metabolite of NAD+ with intracellular Ca2+–mobilizing activity. J. Biol. Chem. 1989;264:1608–1615.

Frohman MA, Dush MK, Martin GR. Rapid production of full–length cDNAs from rare transcripts: amplification using a single gene–specific oligonucleotide primer. Proc. Natl. Acad. Sci. USA 1988;85:8998–9002.

Clapper DL, Walseth TF, Dargie PJ, Lee HC. Pyridine nucleotide metabolites stimulate calcium release from sea urchin egg microsomes desensitized to inositol triphosphate. J. Biol. Chem. 1987;262:9561–9568.

Muller HM, Muller CD, Schuber F. NAD+ glycohydrolase, an ecto–enzyme of calf spleen cells. Biochem. J 1983;212(2):459–464.

Falk W, Goodwin RH Jr, Leonard EJ. A 48–well micro chemotaxis assembly for rapid and accurate measurement of leukocyte migration. J. Immunol. Methods 1980;33:239–247.

Abdallah MA, Biellmann JF, Nordstrom B, Branden CI. The conformation of adenosine diphoshoribose and 8–bromadenosine diphoshoribose when bound to liver alcohol dehydrogenase. Eur. J. Biochem. 1975;50:475–481.

Proteins that regulate CD38 enzyme activity (screens will identify compounds that activate or inactivate these proteins)

| | | |
|---|---|---|
| Consensus | GGAAAGAACG TAGACATATA TTGTTATATA GATTTGTTCA GTTATTTTTC | 50 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | GGAAAGAACG TAGACATATA TTGTTATATA GATTTGTTCA GTTATTTTTC | 50 |
| Consensus | ACAATCTTTT AATTCAAATA ATGATGAACG TAATATTGTT TCTTACTTTA | 100 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | ACAATCTTTT AATTCAAATA ATGATGAACG TAATATTGTT TCTTACTTTA | 100 |
| Consensus | TCAAATATTT TTGTCTTTAA CTCTGCACAA CATCAAATAA ACTTACTTAG | 150 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | TCAAATATTT TTGTCTTTAA CTCTGCACAA CATCAAATAA ACTTACTTAG | 150 |
| Consensus | TGAAATAGTA CAATCACGAT GTACTCAGTG GAAGGTTGAA CATGGAGCTA | 200 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | TGAAATAGTA CAATCACGAT GTACTCAGTG GAAGGTTGAA CATGGAGCTA | 200 |
| Consensus | CTAATATAAG TTGTAGTGAG ATCTGGAATT CATTTGAAAG CATTTTACTT | 250 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | CTAATATAAG TTGTAGTGAG ATCTGGAATT CATTTGAAAG CATTTTACTT | 250 |
| Consensus | TCAACTCATA CTAAATCAGC ATGTGTTATG AAATCAGGGT TATTCGATGA | 300 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | TCAACTCATA CTAAATCAGC ATGTGTTATG AAATCAGGGT TATTCGATGA | 300 |
| Consensus | TTTTGTTTAT CAATTGTTTG AATTGGAACA CAACAACAA CAGCGACACC | 350 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | TTTTGTTTAT CAATTGTTTG AATTGGAACA CAACAACAA CAGCGACACC | 350 |
| Consensus | ACACAATTCA AACGGAACAA TACTTCCATT CTCAAGTGAT GAACATCATT | 400 |
| EST AW017229 comp | ---------- ---------- ---------- ---------- ---------- | |
| EST AI067047 comp | ---------- ---------- ---------- ---------- ---------- | |
| EST N20756 | ---------- ---------- ---------- ---------- ---------- | |
| SM38 | ACACAATTCA AACGGAACAA TACTTCCATT CTCAAGTGAT GAACATCATT | 400 |
| Consensus | CGTGGAATGT GTAAACGTCT TGGAGTATGT CGTTCTCTAG AAACTACATT | 450 |
| EST AW017229 comp | ---------- ---------- ---------- ---------- ---------- | |
| EST AI067047 comp | ---------- ---------- ---------- ---------- ---------- | |
| EST N20756 | ---------- ---------- -GGAGTATGT CGTTCTCTAG AAACTACATT | 29 |
| SM38 | CGTGGAATGT GTAAACGTCT TGGAGTATGT CGTTCTCTAG AAACTACATT | 450 |

Figure 13B

```
Consensus         TCCAGGATAT CTGTTTGATG AATTGAATTG GTGTAATGGC AGTTTAACAG    500
EST AW017229 comp ---------- ---------- ---------- ---------- ----------
EST AI067047 comp ---------- ---------- ---------- ---------- ----------
EST N20756        TCCAGGATAT CTGTTTGATG AATTGAATTG GTGCAATGGC AGTTTAACAG     79
SM38              TCCAGGATAT CTGTTTGATG AATTGAATTG GTGTAATGGC AGTTTAACAG    500

Consensus         GCAACACAAA ATACGGGACT GTATGTGGAT GCGATTATAA AAGTAATGTT    550
EST AW017229 comp ---------- ---------- ---------- ---------- ----------
EST AI067047 comp ---------- ---------- ---------- ---------- ----------
EST N20756        GCAACACAAA ATACGGGACT GTATGTGGAT GCGATTATAA AAGTAATGTT    129
SM38              GCAACACAAA ATACGGGACT GTATGTGGAT GCGATTATAA AAGTAATGTT    550

Consensus         GTTCATGCGT TCTGGCAAAG TGCTTCGGCT GAGTATGCCA GGAGAGCATC    600
EST AW017229 comp ---------- ---------- ------GGCT GAGTATGCCA GGAGAGCATC     24
EST AI067047 comp ---------- ---------- ---------- ---------- ----------
EST N20756        GTTCATGCGT TCTGGCAAAG TGCTTCGGCT GAGTATGCCA GGAGAGCATC    179
SM38              GTTCATGCGT TCTGGCAAAG TGCTTCGGCT GAGTATGCCA GGAGAGCATC    600

Consensus         TGGTAACATC TTTGTGGTAC TGAATGGCTC GGTCAAAGCT CCATTTAATG    650
EST AW017229 comp TGGTAACATC TTTGTGGTAC TGAATGGCTC GGTCAAAGCT CCATTTAATG     74
EST AI067047 comp ---------- ---------- ---------- ---------- ----------
EST N20756        TGGTAACATC TTTGTGGTAC TGAATGGCTC GGTCAAAGCT CCATTTAATG    229
SM38              TGGTAACATC TTTGTGGTAC TGAATGGCTC GGTCAAAGCT CCATTTAATG    650

Consensus         AAAATAAAAC TTTTGGAAAA ATAGAACTAC CATTGGTTAA AACATCCTCG    700
EST AW017229 comp AAAATAAAAC TTTTGGAAAA ATAGAACTAC CATT-GTTAA AACATCCTCG    123
EST AI067047 comp ---------- ---------- ---------- ---------- ----------
EST N20756        AAAATAAAAC TTTTGGAAAA ATAGAACTAC CATTGGTTAA AACATCCTCG    279
SM38              AAAATAAAAC TTTTGGAAAA ATAGAACTAC CATTG-TTAA AACATCCTCG    699

Consensus         AGTACAACAA TTAACAGTGA AATTAGTTCA TAGTTTGGAA GATGTAAATA    750
EST AW017229 comp AGTACAACAA TTAACAGTGA AATTAGTTCA TAGTTTGGAA GATGTAAATA    173
EST AI067047 comp ---------- ---------- ---------- ---------- ----------
EST N20756        A--------- ---------- ---------- ---------- ----------    280
SM38              AGTACAACAA TTAACAGTGA AATTAGTTCA TAGTTTGGAA GATGTAAATA    749

Consensus         ACCGACAAAC ATGTGAATCG TGGAGTCTGC AAGAACTTGC AAACAAGCTG    800
EST AW017229 comp ACCGACAAAC ATGTGAATCG TGGAGTCTGC AAGAACTTGC AAACAAGCTG    223
EST AI067047 comp ---------- ---------- ---------- ---------- ----------    280
EST N20756        ---------- ---------- ---------- ---------- ----------
SM38              ACCGACAAAC ATGTGAATCG TGGAGTCTGC AAGAACTTGC AAACAAGCTG    799

Consensus         AACTCTGTAC ATATTCCTTT TCGTTGCATT GACGATCCTT TAGAGTTCAG    850
EST AW017229 comp AACTCTGTAC ATATTCCTTT TCGTTGCATT GACGATCCTT TAGAGTTCAG    273
EST AI067047 comp ---------- ---------- ---------- ---------- ----------    280
EST N20756        ---------- ---------- ---------- ---------- ----------
SM38              AACTCTGTAC ATATTCCTTT TCGTTGCATT GACGATCCTT TAGAGTTCAG    849

Consensus         ACATTATCAA TGCATTGAAA ATCCTGGCAA ACAACTATGT CAGTTTTCAG    900
EST AW017229 comp ACATTATCAA TGCATTGAAA ATCCTGGCAA ACAACTATGT CAGTTTTCAG    323
EST AI067047 comp ---------- ---ATTGAAA ATCATGGCAA ACAACTATGT CAGTTTTCAG     37
EST N20756        ---------- ---------- ---------- ---------- ----------    280
SM38              ACATTATCAA TGCATTGAAA ATCCTGGCAA ACAACTATGT CAGTTTTCAG    899
```

Figure 13C

| | | |
|---|---|---|
| Consensus | CTTCGACGAG GTCAAACGTC GAGACATTAC TCATACTTTT TCCGCTAGTC | 950 |
| EST AW017229 comp | CTTCGACGAG GTCAAACGTC GAGACATTAC TCATACTTTT TCCGCTAGTC | 373 |
| EST AI067047 comp | CTTCGACGAG GTCAAACGTC GAGACATTAC TCATACTTTT TCCGCTAGTC | 87 |
| EST N20756 | ---------- ---------- ---------- ---------- ---------- | 280 |
| SM38 | CTTCGACGAG GTCAAACGTC GAGACATTAC TCATACTTTT TCCGCTAGTC | 949 |
| | | |
| Consensus | ATTTGTTTAA CTTTTTATAC TTCCATGAAT TGAAATAACT TTTCAGAACT | 1000 |
| EST AW017229 comp | ATTTGTTTAA CTTTTTATAC TTCCATGAAT TGAAATAACT TTTCAGAACT | 423 |
| EST AI067047 comp | ATTTGTTTAA CTTTTTATAC TTCCATGAAT TGAAATAACT TTTCAGAACT | 137 |
| EST N20756 | ---------- ---------- ---------- ---------- ---------- | 280 |
| SM38 | ATTTGTTTAA CTTTTTATAC TTCCATGAAT TGAAATAACT TTTCAGAACT | 999 |
| | | |
| Consensus | AAACTTTGAA CAGAGAAAGA GAACAATGAT AATAAAGGAA TAGGMCATTA | 1050 |
| EST AW017229 comp | AAACTTTGAA CAGAGAAAGA GAACAATGAT AATAAAGGAA TAGGCCATTA | 473 |
| EST AI067047 comp | AAACTTTG-- ---------- ---------- ---------- ---------- | 145 |
| EST N20756 | ---------- ---------- ---------- ---------- ---------- | 280 |
| SM38 | AAACTTTGAA CAGAGAAAGA GAACAATGAT AATAAAGGAA TAGGACATTA | 1049 |

Figure 14

```
GGAAAGAACGTAGACATATATTGTTATATAGATTTGTTCAGTTATTTTTCACAATCTTTTAATTCAAATA    70
 E  R  T  .  T  Y  I  V  I  .  I  C  S  V  I  F  H  N  L  L  I  Q  I

ATGATGAACGTAATATTGTTTCTTACTTTATCAAATATTTTTGTCTTTAACTCTGCACAACATCAAATAA   140
 M  M  N  V  I  L  F  L  T  L  S  N  I  F  V  F  N  S  A  Q  H  Q  I

ACTTACTTAGTGAAATAGTACAATCACGATGTACTCAGTGGAAGGTTGAACATGGAGCTACTAATATAAG   210
 N  L  L  S  E  I  V  Q  S  R  C  T  Q  W  K  V  E  H  G  A  T  N  I  S

TTGTAGTGAGATCTGGAATTCATTTGAAAGCATTTTACTTTCAACTCATACTAAATCAGCATGTGTTATG   280
 C  S  E  I  W  N  S  F  E  S  I  L  L  S  T  H  T  K  S  A  C  V  M

AAATCAGGGTTATTCGATGATTTTGTTTATCAATTGTTTGAATTGGAACAACAACAACAACAGCGACACC   350
 K  S  G  L  F  D  D  F  V  Y  Q  L  F  E  L  E  Q  Q  Q  Q  Q  R  H

ACACAATTCAAACGGAACAATACTTCCATTCTCAAGTGATGAACATCATTCGTGGAATGTGTAAACGTCT   420
 H  T  I  Q  T  E  Q  Y  F  H  S  Q  V  M  N  I  I  R  G  M  C  K  R  L

TGGAGTATGTCGTTCTCTAGAAACTACATTTCCAGGATATCTGTTTGATGAATTGAATTGGTGTAATGGC   490
 G  V  C  R  S  L  E  T  T  F  P  G  Y  L  F  D  E  L  N  W  C  N  G

AGTTTAACAGGCAACACAAAATACGGGACTGTATGTGGATGCGATTATAAAAGTAATGTTGTTCATGCGT   560
 S  L  T  G  N  T  K  Y  G  T  V  C  G  C  D  Y  K  S  N  V  V  H  A

TCTGGCAAAGTGCTTCGGCTGAGTATGCCAGGAGAGCATCTGGTAACATCTTTGTGGTACTGAATGGCTC   630
 F  W  Q  S  A  S  A  E  Y  A  R  R  A  S  G  N  I  F  V  V  L  N  G  S

GGTCAAAGCTCCATTTAATGAAAATAAAACTTTTGGAAAAATAGAACTACCATTGTTAAAACATCCTCGA   700
 V  K  A  P  F  N  E  N  K  T  F  G  K  I  E  L  P  L  L  K  H  P  R

GTACAACAATTAACAGTGAAATTAGTTCATAGTTTGGAAGATGTAAATAACCGACAAACATGTGAATCGT   770
 V  Q  Q  L  T  V  K  L  V  H  S  L  E  D  V  N  N  R  Q  T  C  E  S

GGAGTCTGCAAGAACTTGCAAACAAGCTGAACTCTGTACATATTCCTTTTCGTTGCATTGACGATCCTTT   840
 W  S  L  Q  E  L  A  N  K  L  N  S  V  H  I  P  F  R  C  I  D  D  P  L

AGAGTTCAGACATTATCAATGCATTGAAAATCCTGGCAAACAACTATGTCAGTTTTCAGCTTCGACGAGG   910
 E  F  R  H  Y  Q  C  I  E  N  P  G  K  Q  L  C  Q  F  S  A  S  T  R

TCAAACGTCGAGACATTACTCATACTTTTTCCGCTAGTCATTTGTTTAACTTTTTATACTTCCATGAATT   980
 S  N  V  E  T  L  L  I  L  F  P  L  V  I  C  L  T  F  Y  T  S  M  N

GAAATAACTTTTCAGAACTAAACTTTGAACAGAGAAAGAGAACAATGATAATAAAGGAATAGGACATTAA  1050
 N  N  F  S  E  L  N  F  E  Q  R  K  R  T  M  I  I  K  E  .  D  I  N

TGAAAAAAAAAAAAAAAAAAAAAA  1073
 E  K  K  K  K  K  K
```

Figure 15 A-B

A.

```
Consensus     M.........  .L.......S  ....I......  L.......RC.  ..........     50
Aplysia cd38p MSPVAIVACV  CLAVTLTRIS  PSEAIFPTPE   LQNVFLGRQK   DYEITRYLTI     50
SM38p         M--MNVILFL  TLSNIFVFNS  AQHQI---NL   LSEIVQSRCT   QWKVEH----     41

Consensus     ........C..  .W..F......  ....K..C..   ..G...DF..   ..........    100
Aplysia cd38p LPRVKSDCRA  LWTNFFKAFS  F---KAPCNL   DLGSYKDFFQ   RAQQTLPKNK     97
SM38p         -GATNISCSE  IWNSEESILL  STHTKSACVM   KSGLFDDFVY   QLFELEQQQQ     90

Consensus     ..........  ..........  ..........   LE.T.PGY     ....L.WC..    150
Aplysia cd38p VMFWSGVYDE  --AHDF----  ADDGRKYI---  -TLEDTLPGY   MLNSLVWCGQ    138
SM38p         QRHHTIQTEQ  YFHSQVMNII  RGMCKRLGVC   RSLETTFPGM   LFDELNWCNG    140

Consensus     ..........  VC....D...  .....FW..A   S..YA..A.G   ........GS.   200
Aplysia cd38p RDKPGFNQK-  VCPDFKDCPV  QARESFWGTA   SSSYAHSAEG   DVTYMVDGSN    187
SM38p         SLTGNTKYGT  VC--GCDYKS  NVVHAFWQSA   SAEYARRASG   NIFVVLNGS-    186

Consensus     ..........  .FGK.ELP.L  ....V......  ...H.L....   ....C...SL    250
Aplysia cd38p PKVPAYRPDS  FFGKYELPNL  TNK-VTKVKV   IVLHQLGQKI   I-ERCGAGSL    235
SM38p         -VKAPFNENK  TFGKIELPLL  KHPRVQQLTV   KLVHSLEDVN   NRQTCESWSL    236

Consensus     ..L.......  ...F.C...P  .......C..   NP....CQ..   ..........    300
Aplysia cd38p LDLEMVVKAK  KFGFDCVENP  KSVLFLLCAD   NPNAREGQLA   KRYYRIA---    282
SM38p         QELANKLNSV  HIPFRCIDDP  LEFRHYQGIE   NPGKQLCQFS   ASTRSNVETL    286

Consensus     ..........  .......                                              317
Aplysia cd38p ----------  -------                                              282
SM38p         LILFPLVICL  TFYTSMN                                              303
```

B.

```
Consensus     M.........  ..........  ..........   ..IL...L..   .......Q..     50
Human CD38    MANCEFSPVS  GDKPCCRLSR  RAQLCLGVSI   LVLILVVVLA   VVVPRWRQQW     50
SM38p         M---------  ----------  ----------   MNVILFLTLS   NIFVFNSAQ-     20

Consensus     ..........  E.V..RC...  ..........   .C...W..F.   .....S.H.K.   100
Human CD38    SGPGTTKRFP  ETVLARCVKY  TEIHPEMRHV   DCQSVWDAFK   GAFIS---KH     97
SM38p         ---HQINLLS  EIVQSRCTQW  -KVEHGATNI   SCSEIWNSFE   SILLSTHTKS     66

Consensus     .C........  ....YQ....  ..........   ..........   .S........    150
Human CD38    PCNITEED--  ---MQPLMKL  GTQTVPCNKI   L----LWSRI   KDLAHQFTQV    138
SM38p         ACVMKSGLFD  DFVYQLFELE  QQQQQRHHTI   QTEQYFHSQV   MNIIRGMCKR    116

Consensus     ......LE.T  ..GYL.D.L.  WC....T...   .Y...C....   ..C....N.V    200
Human CD38    QRDMFTLEDT  LLGYLADDLT  WCGEFNTSKI   NYQS-CPDWR   KDC--SNNPV    185
SM38p         LGVCRSLETT  FPGYLFDELN  WCNGSLTGNT   KYGTVQG---   --CDYKSNVV    161

Consensus     ..FW...S..  .A..A.....  V.LNGS....   F..N.TFG..   E...L....V    250
Human CD38    SVFWKTVSRR  FAEAACDVVH  VMLNGSRSKI   FDKNSTFGSV   EVHNLQPEKV    235
SM38p         HAFWQSASAE  YARRASGNIF  VVLNGSVKAP   FNENKTFGKI   ELPLLKHPRV    211

Consensus     Q.L.....H.  ......R..C  ......EL..   .......I.F.  .C........    300
Human CD38    QTLEAWVIHG  GRE-DSRDLC  QDPTIKELES   IISKRNIQFS   CKNIYRPDKF    284
SM38p         QQLTVKLVHS  LEDVNNRQTC  ESWSLQELAN   KLNSVHIPFR   CIDDPLEFRH    261

Consensus     .QC..NP...  .C........  ..........   ..........   TS..          342
Human CD38    LQCVKNPEDS  SC--------  ----------   ----------   TS EI         300
SM38p         YQGIENPGKQ  LCQFSASTRS  NVETLLILFP   LVICLTFYTS   MN            303
```

```
MMNVILFLTL SNIFVFNSAQ HQINLLSEIV QSRCTQWKVE HGATNISCSE   50
IWNSFESILL STHTKSACVM KSGLFDDFVY QLFELEQQQQ QRHHTIQTEQ  100
YFHSQVMNII RGMCKRLGVC RSLETTFPGY LFDELNWCNG SLTGNTKYGT  150
VCGCDYKSNV VHAFWQSASA EYARRASGNI FVVLNGSVKA PFNENKTFGK  200
IELPLLKHPR VQQLTVKLVH SLEDVNNRQT CESWSLQELA NKLNSVHIPF  250
RCIDDPLEFR HYQCIENPGK QLCQFSASTR SNVETLLILF PLVICLTFYT  300
SMN                                                    303
```

Figure 16

```
ATGATGAAYG TNATHYTNTT YYTNACNYTN WSNAAYATHT TYGTNTTYAA    50
YWSNGCNCAR CAYCARATHA AYYTNYTNWS NGARATHGTN CARWSNMGNT   100
GYACNCARTG GAARGTNGAR CAYGGNGCNA CNAAYATHWS NTGYWSNGAR   150
ATHTGGAAYW SNTTYGARWS NATHYTNYTN WSNACNCAYA CNAARWSNGC   200
NTGYGTNATG AARWSNGGNY TNTTYGAYGA YTTYGTNTAY CARYTNTTYG   250
ARYTNGARCA RCARCARCAR CARMGNCAYC AYACNATHCA RACNGARCAR   300
TAYTTYCAYW SNCARGTNAT GAAYATHATH MGNGGNATGT GYAARMGNYT   350
NGGNGTNTGY MGNWSNYTNG ARACNACNTT YCCNGGNTAY YTNTTYGAYG   400
ARYTNAAYTG GTGYAAYGGN WSNYTNACNG GNAAYACNAA RTAYGGNACN   450
GTNTGYGGNT GYGAYTAYAA RWSNAAYGTN GTNCAYGCNT TYTGGCARWS   500
NGCNWSNGCN GARTAYGCNM GNMGNGCNWS NGGNAAYATH TTYGTNGTNY   550
TNAAYGGNWS NGTNAARGCN CCNTTYAAYG ARAAYAARAC NTTYGGNAAR   600
ATHGARYTNC CNYTNYTNAA RCAYCCNMGN GTNCARCARY TNACNGTNAA   650
RYTNGTNCAY WSNYTNGARG AYGTNAAYAA YMGNCARACN TGYGARWSNT   700
GGWSNYTNCA RGARYTNGCN AAYAARYTNA AYWSNGTNCA YATHCCNTTY   750
MGNTGYATHG AYGAYCCNYT NGARTTYMGN CAYTAYCART GYATHGARAA   800
YCCNGGNAAR CARYTNTGYC ARTTYWSNGC NWSNACNMGN WSNAAYGTNG   850
ARACNYTNYT NATHYTNTTY CCNYTNGTNA THTGYYTNAC NTTYTAYACN   900
WSNATGAAY                                                909
```

Figure17

METHODS FOR IDENTIFYING COMPOUNDS THAT INHIBIT CD38 ACTIVITY

This application claims benefit of U.S. provisional application 60/241,065 filed Oct. 17, 2000.

1. INTRODUCTION

The present invention relates to methods for modulating the migratory activity of cells expressing CD38 for the treatment of disorders including, but not limited to, inflammation, ischemia, asthma, autoimmune disease, diabetes, arthritis, allergies, infection with pathogenic organisms, such as parasites, and transplant rejection. Such cells include, for example, neutrophils, lymphocytes, eosinophils, macrophages and dentritic cells. The invention further relates to drug screening assays designed to identify compounds that modulate the ADP-ribosyl cyclase activity of CD38 and the use of such compounds in the treatment of disorders involving CD38 modulated cell migration. Additionally, the invention relates to the isolation and characterization of a CD38 homologue from the parasitic flatworm, Schistosoma mansoni. The identification of such a homologue, referred to herein as SM38, provides compositions and assays designed to screen for related enzymes in pathogenic organisms as well as compositions and assays to screen for compounds that modulate the activity and/or expression of SM38. Such compounds can be used to treat pathogenic disorders resulting from infection with such parasites. The invention is based on the discoveries that CD38 ADP-ribosyl cyclase activity is required for chemotaxis and that S. mansoni expresses a CD38 homologue that can regulate calcium responses in the parasite.

2. BACKGROUND OF INVENTION

Hematopoietically-derived cells, including cells such as neutrophils, monocytes, dendritic cells, eosinophils and lymphocytes, are important cellular mediators of the inflammatory response and respond to soluble inflammatory mediators by migration to the site of tissue injury or infection where the newly arrived cells perform their effector functions.

Neutrophils which represent 40–50% of the circulating leukocyte population are particularly important to both immunity and inflammation. Neutrophils are normally quiescent cells but upon stimulation can mediate a variety of different inflammatory activities. A large number of different agents are capable of activating neutrophils and this activation is normally mediated by binding of the activating agent to specific receptors expressed on the surface of neutrophils. Once activated, the neutrophils are capable of binding to endothelial cells and migrating to the site of tissue damage, a pathogen or a foreign material. Similarly, eosinophils are also potent inflammatory effector cells, although these cells are most often associated with allergic diseases such as asthma. Like neutrophils, eosinophils have a potent armory of proinflammatory molecules that can initiate and maintain inflammatory responses.

Once at the inflammatory site, recruited cells such as eosinophils and neutrophils induce further inflammation by releasing inflammatory products and recruiting other hematopoietically-derived cells to the site. In some cases, the inflammatory response mediated by the specifically recruited hematopoietically-derived cells protects the host from morbidity or mortality by eliminating the infectious agent. In other cases (i.e., autoimmunity, ischemia/reperfusion, transplantation, allergy), the inflammatory response further damages the tissue resulting in pathology. Thus, agents which alter inflammation or recruitment of cells may be useful in controlling pathology.

Although CD38 expression was at first believed to be restricted to cells of the B cell lineage, subsequent experiments by a number of groups have demonstrated that CD38 is widely expressed on both hematopoietic and non-hematopoietically-derived cells. Homologues of CD38 have also been found to be expressed in mammalian stromal cells (Bst-1) and in cells isolated from the invertebrate Aplysia californica (ADP-ribosyl cyclase enzyme) (Prasad GS, 1996, nature Structural Biol 3:957–964)

More recently, CD38 was shown to be a multifunctional ecto-enzyme with $NAD^+$ glycohydrolase activity and ADP-ribosyl cyclase activity, enabling it to produce nicotinamide, ADP-ribose (ADPR), cyclic-ADPR (cADPR) and nicotinic acid adenine dinucleotide phosphate (NAADP) from its substrates $NAD^+$ and NADP (Howard et al., 1993 Science 252:1056–1059; Lee et al., 1999 Biol. Chem. 380;785–793). Two of the metabolites produced by CD38, cADPR and NAADP, have been shown to induce the release of intracellular calcium in cells isolated from tissues of plants, invertebrates and mammals, suggesting that these metabolites may be global regulators of calcium responses (Lee et al., 1999 Biol. Chem. 380;785–793).

Both cADPR and NAADP are known to induce calcium release from calcium stores that are distinct from those controlled by $Ip^3$ receptors (Clapper, D L et al., 1987, J. Biological Chem. 262:9561–9568). Instead, cADPR is believed to regulate calcium release from ryanodine receptor regulated stores, as agonists of ryanodine receptors sensitize cADPR mediated calcium release and antagonists of ryanodine receptors block cADPR dependent calcium release (Galione A et al., 1991, Science 253:143–146). Thus, it has been proposed that cADPR is likely to regulate calcium responses in tissues such as muscle and pancreas where ryanodine receptors are expressed. Interestingly, it was recently shown that the muscle fibers of the parasitic flatworm, S. mansoni, express ryanodine receptors and that agonists of ryanodine receptors such as caffeine can induce intracellular calcium release and muscle contraction in the parasite (Day et al., 2000 Parasitol 120:417–422; Silva et al., 1998, Biochem. Pharmacol 56:997–1003). In mammalian smooth muscle cells, the calcium release in response to acetylcholine can be blocked not only with ryanodine receptor antagonists, but also with specific antagonists of cADPR such as 8-$NH^2$-cADPR or 8-Br-cADPR (Guse, A H, 1999, Cell. Signal. 11:309–316).

These findings, as well as others, indicate that ryanodine receptor agonists/antagonists including cADPR can regulate calcium responses in cells isolated from species as diverse as helminths to mammals, however, it is unclear whether ADP-ribosyl cyclase enzymes such as CD38 or SM38 are required for the production of cADPR in vivo. Additionally, there has been no direct evidence to link CD38 enzyme activity with downstream responses such as calcium release, proliferation, apoptosis, migration or other effector functions. Thus, despite the high level expression of CD38 on many cell types, no clear defining role for CD38 enzyme activity in immune responses has been established.

3. SUMMARY OF THE INVENTION

The present invention relates to methods for modulating the migratory activity of cells expressing CD38 involving the administration of agonists or antagonists of CD38 enzyme activity, and the cADPR mediated signal transduction pathway, including small molecules, large molecules, and antibodies. The invention also provides for compounds and nucleotide sequences that can be used to modulate CD38 gene expression.

The present invention further relates to the isolation and characterization of a CD38 homologue from the parasitic flatworm *Shistosoma mansoni*, herein referred to as SM38. The identification of such a homologue provides compositions and assays designed to screen for related enzymes in pathogenic micro-organisms (such as helminths) as well as compositions and assays to screen for compounds that modulate the activity of SM38. Such compounds can be used to treat pathogenic disorders resulting from infection with such pathogenic micro-organisms.

The invention relates to assays designed to screen for compounds that modulate the enzymatic activity of CD38 and/or SM38 (CD38/SM38), i.e., compounds that act as agonists and antagonists of CD38 enzyme activity. In addition, the screens of the invention may be used to identify substrates of CD38/SM38 that are converted into antagonists or agonists of signal transduction pathways involving cADPR. The screens of the invention also may be used to directly identify agonists and antagonists of signal transduction pathways involving cADPR.

The invention also relates to assays designed to screen for compounds that modulate CD38/SM38 gene expression. For example, cell-based assays can be used to screen for compounds that modulate CD38/SM38 transcription such as compounds that modulate expression, production or activity of transcription factors involved in CD38/SM38 gene expression; antisense and ribozyme polynucleotides that modulate translation of CD38/SM38 mRNAs and polynucleotides that form triple helical structures with the CD38/SM38 regulatory regions and inhibit transcription of the CD38/SM38 gene.

Identified compounds may be used in the treatment of disorders where the migratory activity of CD38-expressing cells, such as hematopoietically-derived cells, contributes to the development of such disorders. Such disorders include, but are not limited to inflammation, ischemia, asthma, autoimmune disease, diabetes, arthritis, allergies or transplant rejection where inhibition of migratory activity using, for example, CD38 antagonists would be desired. In contrast, in subjects infected with pathogenic microorganisms or immunosuppressed subjects it may be desirable to induce the migratory activity of hematopoietically-derived cells using, for example, agonists of CD38. Additionally, identified compounds may be used to treat pathogenic disorders resulting from infection with pathogenic micro-organisms expressing SM38 or structurally related homologous proteins.

4. BRIEF DESCRIPTION OF THE FIGURES

FIG. 1. Normal Cellular Response to Chemoattractant Signaling. (1) Chemoattractant binds to receptor and initiates signaling. (2) CD38 hydrolyzes NAD and produces cADPR, which facilitates Ca2+ release from internal stores. (3) Ca2+ is released from cADPR-controlled internal stores which activates external Ca2+ channel. (4) Extracellular Ca2+ flows into the cell and allows migration.

Figure 2:
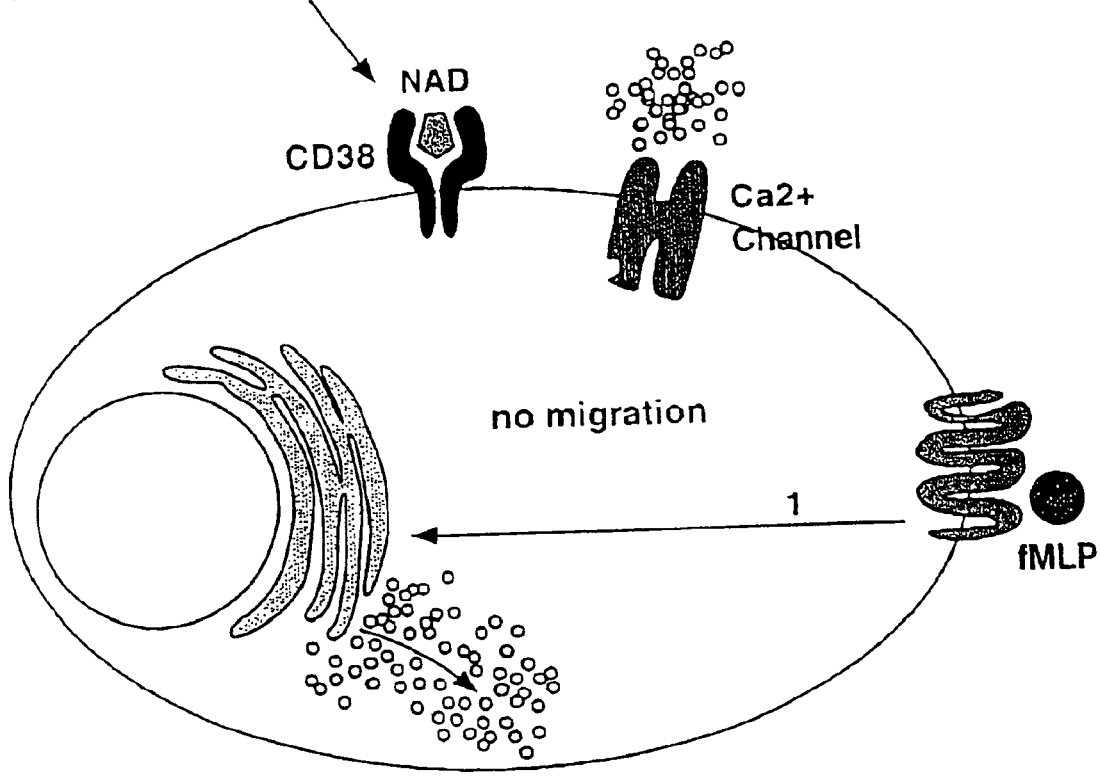

FIG. 2. Inhibitors of cADPR Production by CD38 Prevent Capacitative Ca2+ Entry and Chemoattractant Induced Migration (Screens will identify such compounds). (1) Chemoattractant binds to receptor and initiates signaling. (2) Inhibitor of CD38 prevents either hydrolysis of NAD (enzyme is inactive and no products are made) or specifically inhibits production of cADPR (blocks ADP-ribosyl cyclase activity, but enzyme may not be inactive). (3) Lack of cADPR results in no cADPR-mediated Ca2+ release from internal stores. (4) No capacitative Ca2+ influx and no migration.

Figure 3:
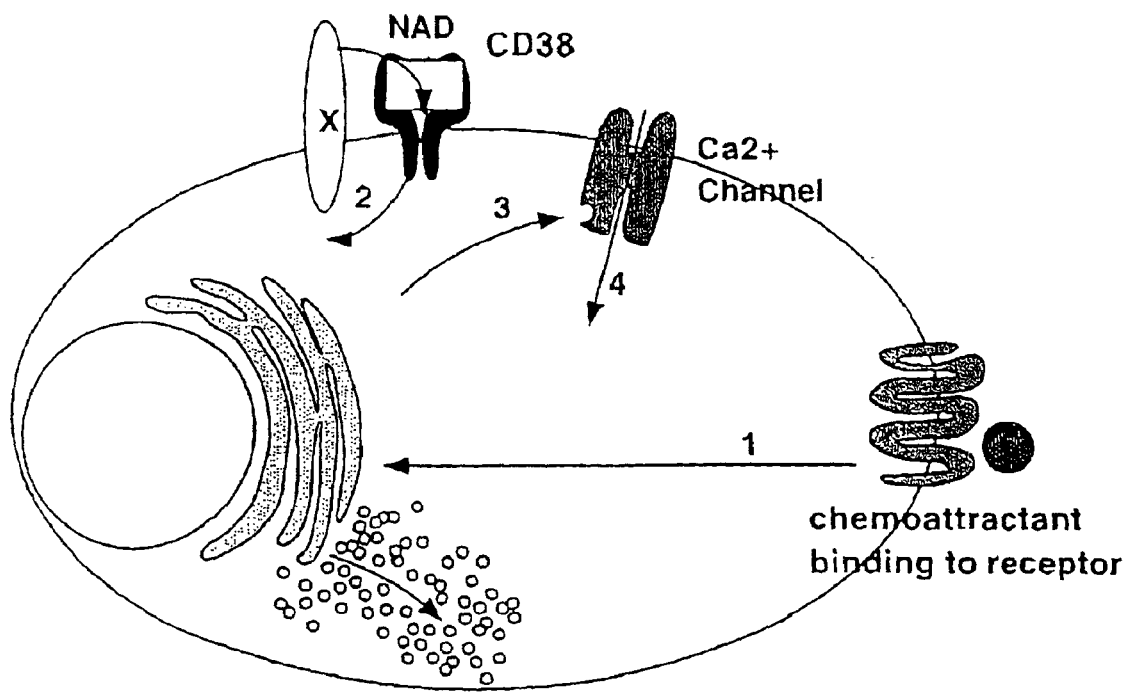

FIG. 3. Proteins that Regulate CD38 Enzyme Activity (Screens will identify compounds that activate or inactivate these proteins). (1) Chemoattractant binds to receptor and initiates signaling. (2) Protein X modifies CD38 and inactivates CD38 enzyme activities. (3) Lack of cADPR results in no cADPR-mediated Ca2+ release from internal stores. (4) No capacitative Ca2+ influx and no migration.

Figure 4:
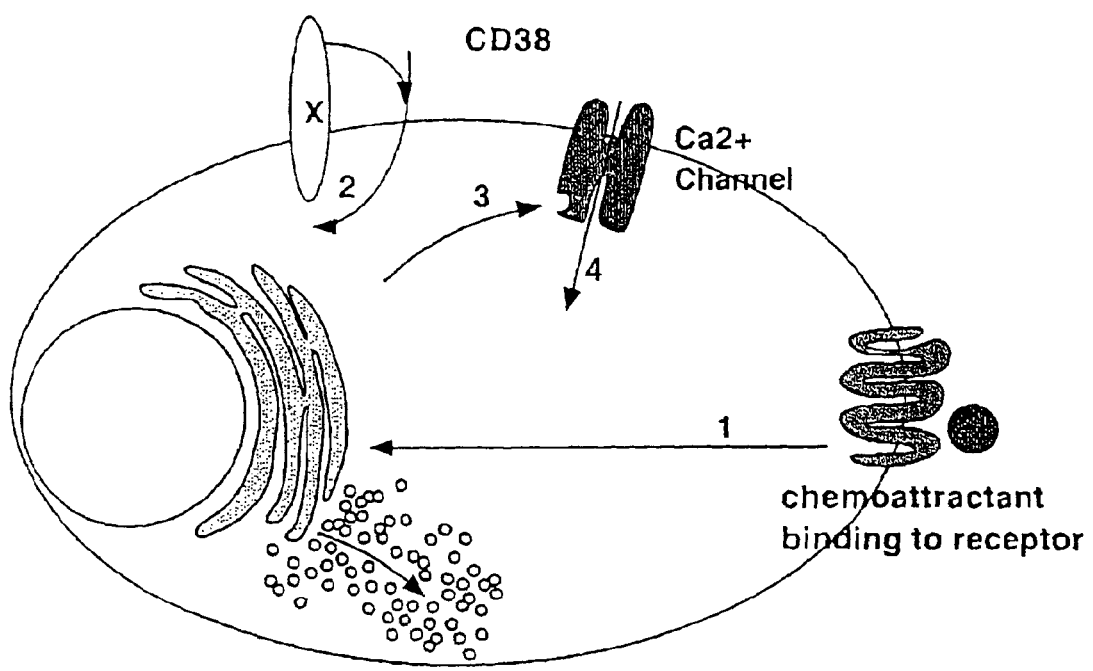

FIG. 4. Proteins that Regulate CD38 Expression (Screens will identify compounds that activate or inactivate these proteins).(1) Chemoattractant binds to receptor and initiates signaling. (2) Protein X represses CD38 gene transcription. (3) Lack of CD38 results in absence of cADPR which results in no cADPR-mediated Ca2+ release from internal stores. (4) No capacitative Ca2+ influx and no migration.

Figure 5:
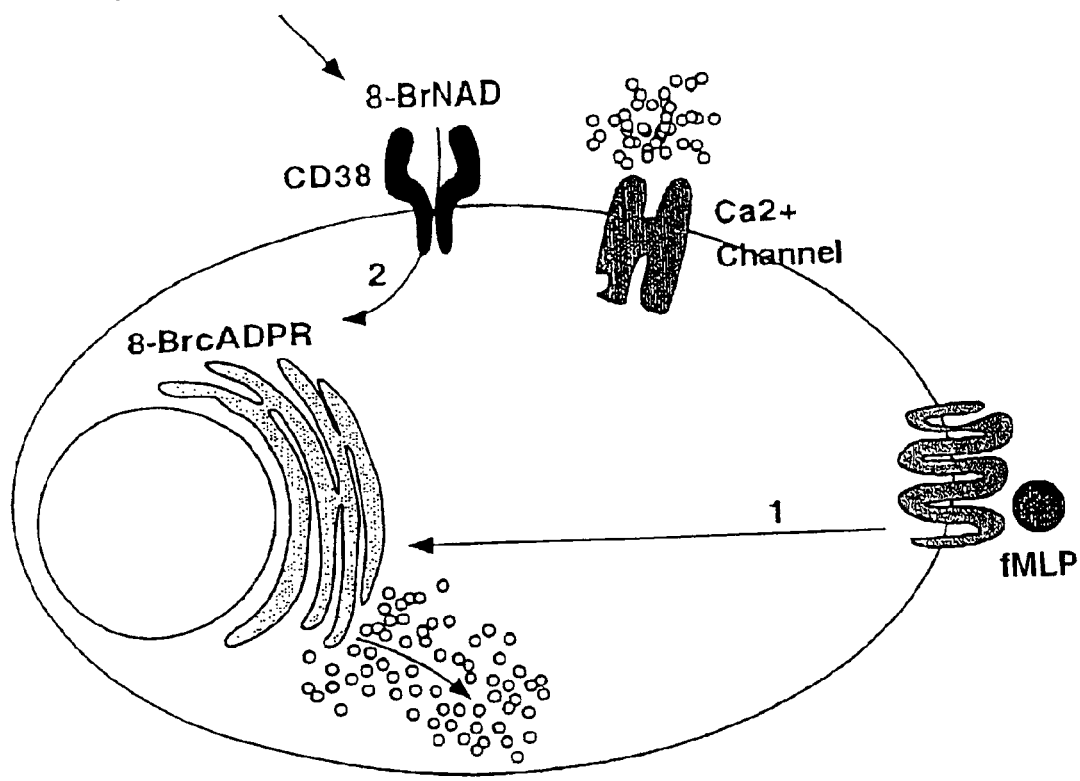

FIG. 5. Alternate Substrates for CD38 may generate inhibitors of cADPR and prevent capacitative Ca2+ release (Screens will identify such compounds). (1) Chemoattractant binds to receptor and initiates signaling. (2) CD38 hydrolyzes modified substrate (8-BrNAD, for example)and produces modified product (8-Br-cADPR, for example) (3) Modified product competitively or non-competitively inhibits cADPR induced Ca2+ release from internal stores. (4) No capacitative Ca2+ influx and no migration.

Figure 6:
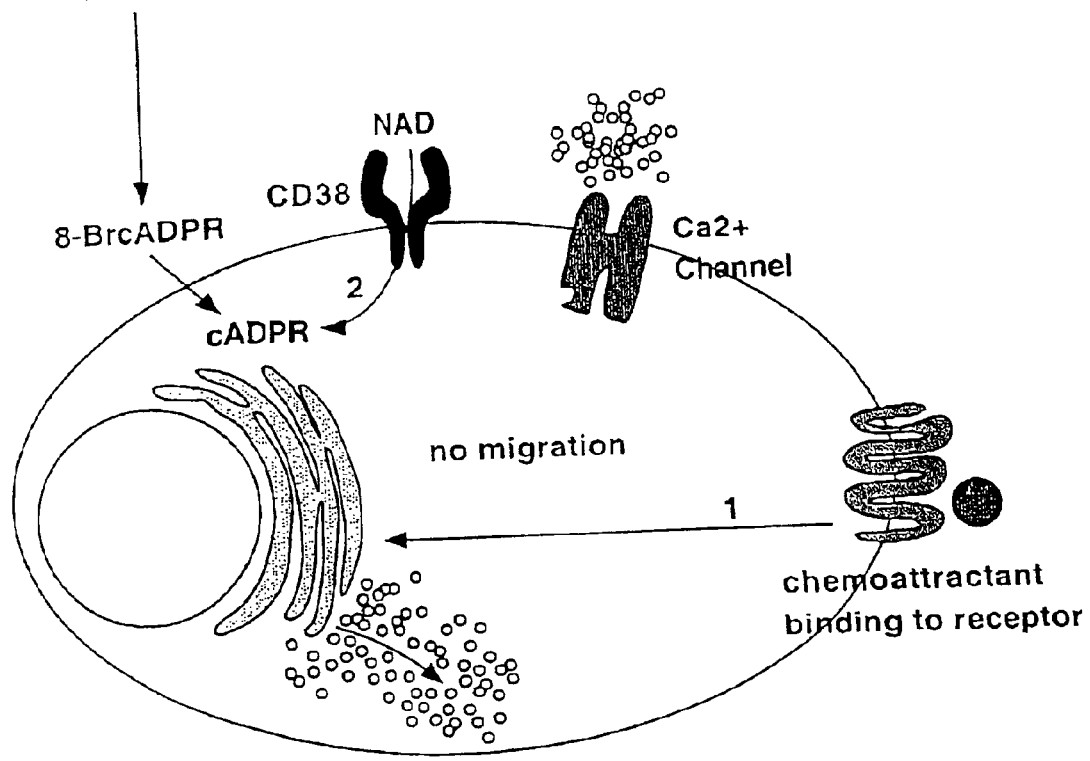

FIG. 6. Inhibitors of cADPR binding block capacitative Ca2+ influx. (1) Chemoattractant binds to receptor and initiates signaling (Screens will identify such compounds). (2) CD38 hydrolyzes NAD and produces cADPR. (3) Inhibitor of cADPR (8-Br cADPR) competitively or non-competitively blocks cADPR induced Ca2+ release from internal stores. (4) No capacitative Ca2+ influx and no migration.

Figure 7:
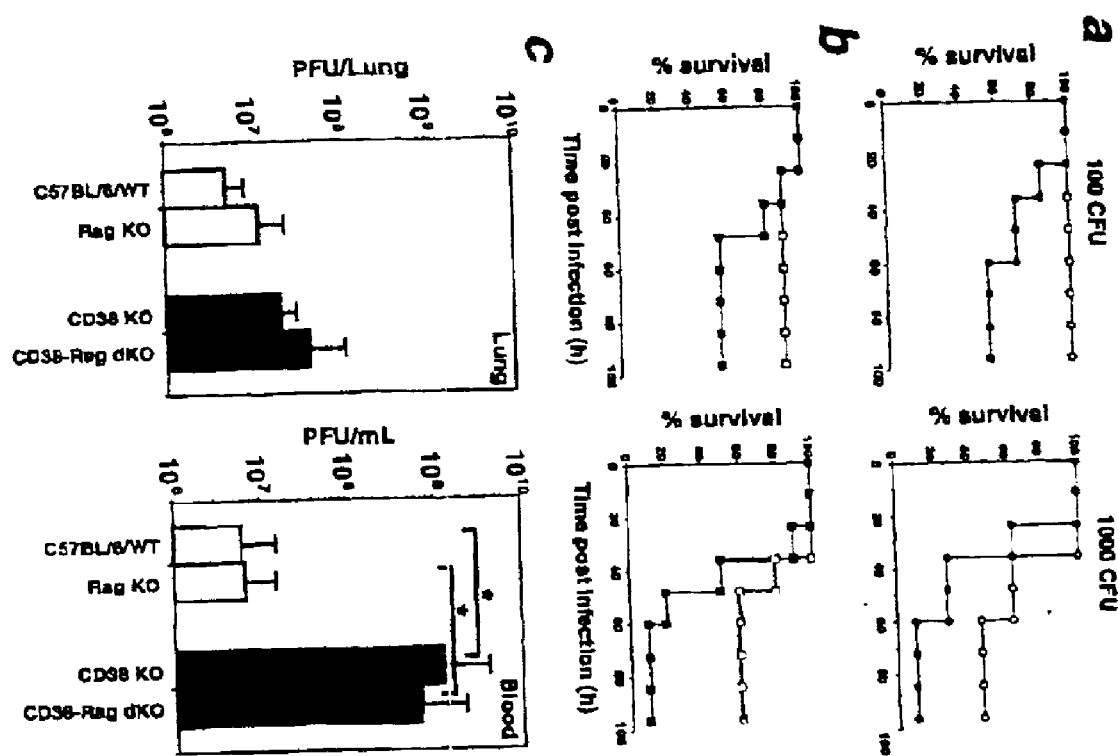

FIG. 7. CD38KO mice are more susceptible to *S. pneumoniae* infection. (a) C57BL/6 WT (open circles) and CD38KO (filled circles) mice were infected intra-tracheally with two doses of *S. pneumoniae*. The survival of infected animals was monitored over the next 4 days. (b) WT mice that had been irradiated and reconstituted with WT bone marrow (open squares) or CD38KO bone marrow (filled squares) were infected with two doses of *S. pneumoniae* and monitored for four days. The data are representative of at least 5 independent experiments. n=10 mice/group. (c) WT or Rag-2 KO (open bars) and CD38KO or CD38-Rag-2 double KO (filled bars) mice were infected intra-tracheally with *S. pneumoniae* and bacterial titers in lung and peripheral blood were determined at 12 hours post-infection. The data are representative of 3 independent experiments. n=10 mice/group. *P<0.001; Student's t test.

Figure 8:
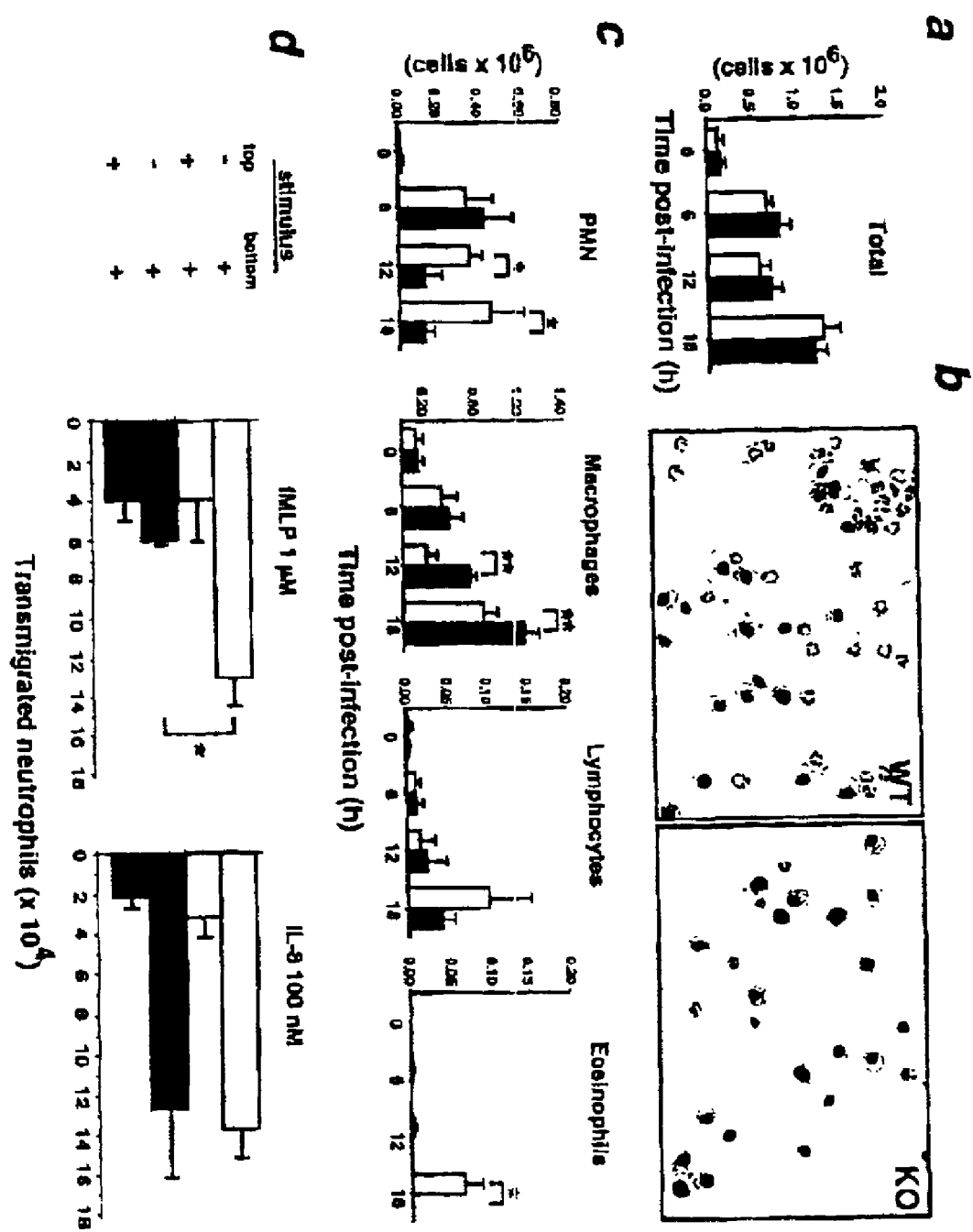

FIG. 8. CD38KO neutrophils are not recruited to the infection site and are unable to chemotax toward bacterially-derived chemoattractants. WT and CD38KO mice were infected intra-tracheally with *S. pneumoniae,* and the cellular infiltrate in the airways was collected and counted (panel a, WT=open bars and CD38KO=closed bars) at multiple timepoints post-infection. (b) The identity and frequency of the infiltrating cells in the lungs of infected WT and CD38KO mice was determined by microscopic examination (400× magnification) and counting of Diff-Quick stained cytocentrifuge preparations. (c) Differential cell counts in the lung lavage of WT (open bars) and CD38KO (closed bars) mice are presented as the mean number of cells ×10⁶±(SE). Similar results were obtained in 5 independent experiments. n=5 mice/group/timepoint. *P<0.0**P=0.01; Student's t Test. (d) Purified bone marrow neutrophils from WT (open bars) and CD38KO mice (filled bars) were tested for their ability to migrate in response to medium, fMLP or IL-8 in a conventional transwell checkerboard chemokinesis/chemotaxis assay. The number of cells migrating to the bottom chamber of the transwell in the absence of any stimulation was not significantly different between CD38KO and WT neutrophils and ranged from 1500–2300 cells (not shown). The number of neutrophils migrating in response to equivalent concentrations of stimuli in both chambers (chemokinesis) and the number of neutrophils migrating in response to a chemotactic gradient (chemotaxis) is shown. The values shown are the mean ±S.E. of four different experiments. *P<0.001; Student's t Test.

Figure 9:
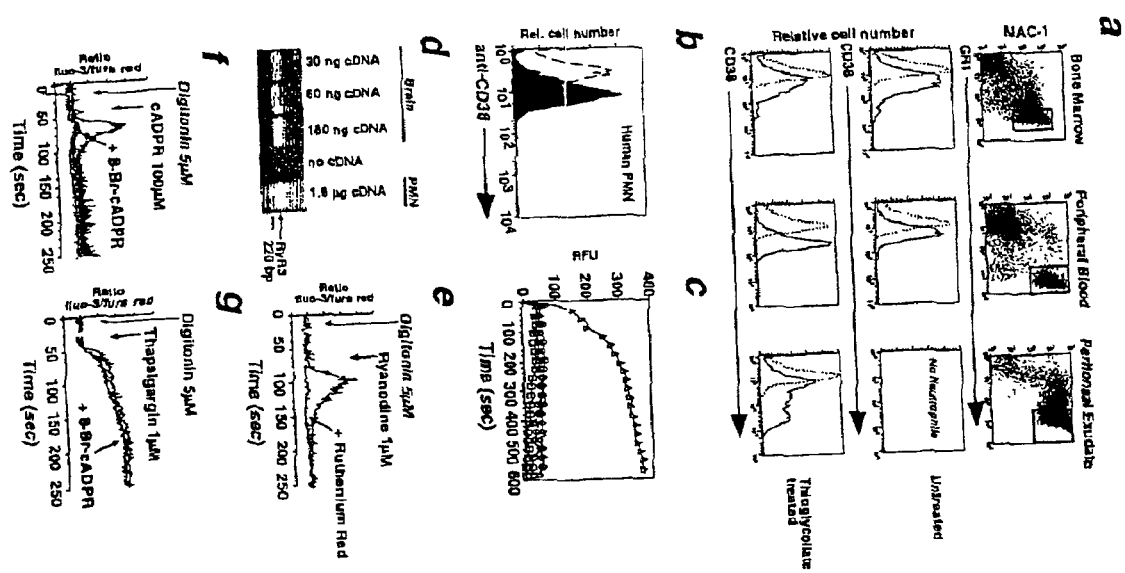

FIG. 9. CD38 expressing neutrophils produce cADPR and release intracellular calcium in response to cADPR and ryanodine. (a) Bone marrow, peripheral blood and peritoneal cavity cells were isolated from WT and CD38KO mice or WT and CD38KO mice that received an intraperitoneal injection of thioglycollate 12 hrs previously. CD38 expression on the Mac-1$^{hi}$GR-1$^{hi}$ neutrophils was analyzed by flow cytometry. Expression of CD38 on WT neutrophils (solid line histogram) and CD38KO neutrophils (dotted line histogram) is shown. (b) CD15+ human peripheral blood neutrophils were assessed for CD38 expression by staining with anti-CD38 mAb (filled histogram) or an isotype control Ab (dotted line). (c) Cyclase activity was measured in WT and CD38KO bone marrow neutrophils. WT or CD38KO neutrophils were incubated alone (WT=circles and CD38KO=squares) or in the presence of NGD (WT=triangles and CD38KO=diamonds) for 10 minutes. The accumulation of the product, cGDPR, was measured fluorometrically. (d) RyR3 mRNA expression levels were determined by RT-PCR. cDNA was isolated from purified WT bone marrow neutrophils (PMN) or brain tissue. The amount of input cDNA is indicated. (e–g) Intracellular free calcium levels were measured by FACS in Fluo-3/Fura Red loaded bone marrow neutrophils. (e) Neutrophils were permeabilized with digitonin and then stimulated with ryanodine in the presence (orange line) or absence (blue line) of ruthenium red. (f) Neutrophils were permeabilized in digitonin and then stimulated with cADPR (blue line), heat inactivated cADPR (green line) or 8-Br-cADPR+cADPR (red line). (g) Neutrophils were stimulated with thapsigargin (blue line) or thapsigargin+8-Br-cADPR (red line). All data in panels e–g are representative of at least three independent experiments.

Figure 10:
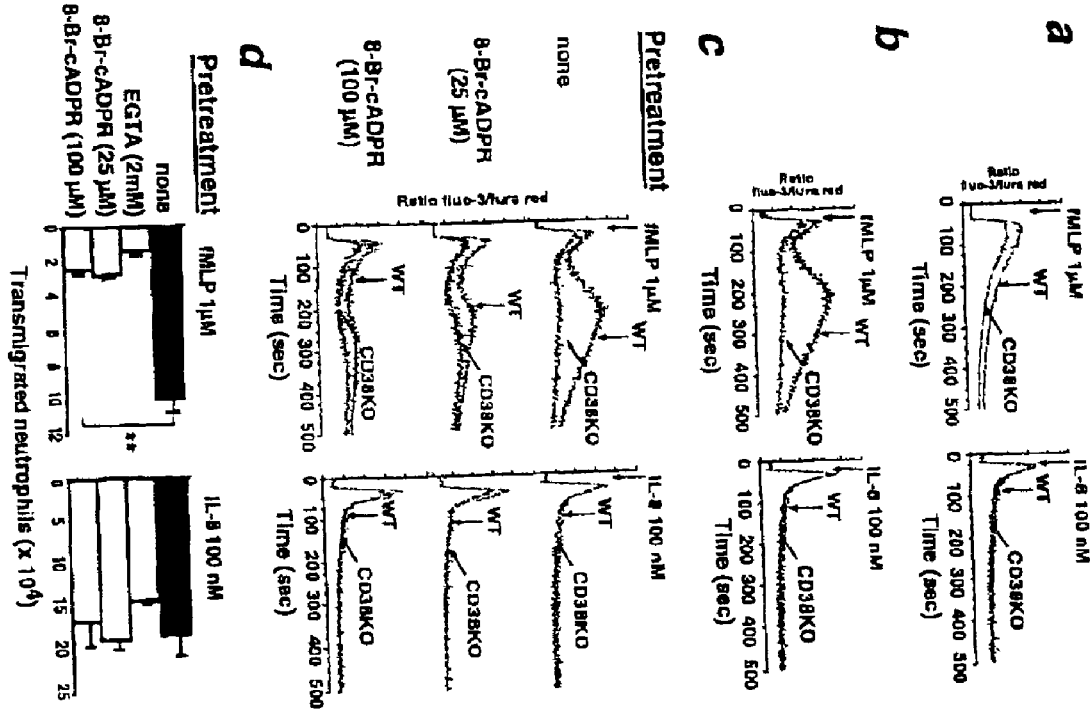

FIG. 10. CD38 catalyzed cADPR regulates intracellular calcium release, extracellular calcium influx and chemotaxis in neutrophils. (a–c) Intracellular free calcium levels were measured by FACS in Fluo-3/Fura Red loaded bone marrow neutrophils. (a) CD38KO (red line) and WT (blue line) neutrophils were stimulated with fMLP or IL-8 in calcium-free buffer. (b) CD38KO (red line) and WT (blue line) neutrophils were stimulated with fMLP or IL-8 in calcium-containing buffer. (c) CD38KO (red line) and WT (blue line) neutrophils were preincubated in calcium-containing medium±8-Br-cADPR and then stimulated with fMLP or IL-8. All data in panels a–c are representative of at least five independent experiments. (d) WT neutrophils were preincubated with medium, EGTA or 8-Br-cADPR and then placed in the top chamber of a transwell that contained fMLP or IL-8 in the bottom chamber. The cells that migrated to the bottom chamber in response to the chemotactic gradient were collected and enumerated by flow cytometry. Values shown are mean ±S.E. from three separate experiments with three wells/experimental condition. **P=0.008; Mann Whitney Rank Sum Test.

Figure 11:
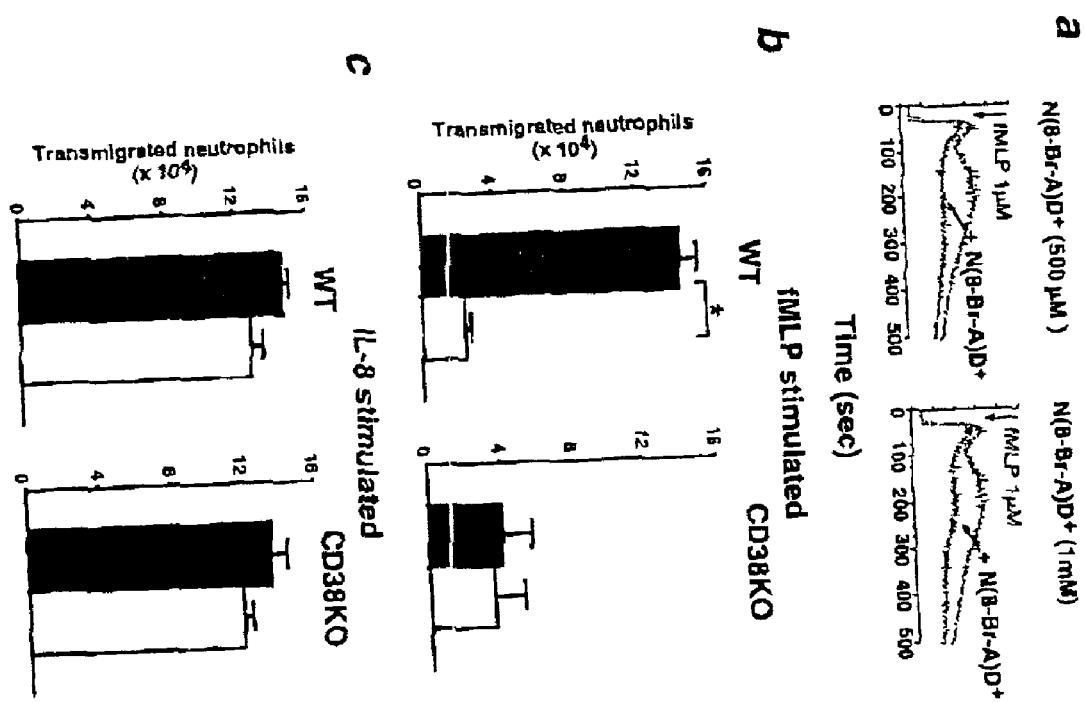

FIG. 11. An NAD+ analogue regulates calcium influx and chemotaxis in fMLP-activated neutrophils. (a) Dye-loaded purified bone marrow neutrophils from WT mice were preincubated in medium (blue line) or increasing concentrations of N(8-Br-A)D+ (red line) and then stimulated with fMLP. Changes in intracellular calcium levels were measured by flow cytometry. The data are representative of three independent experiments. (b–c) WT (left panel) and CD38KO (right panel) neutrophils were preincubated with medium (filled bars) or N(8-Br-A)D+ (open bars) and then placed in the top chamber of a transwell which contained fMLP (panel b) or IL-8 (panel c) in the bottom chamber. The cells that migrated to the bottom chamber in response to the chemotactic gradient were collected and enumerated by flow cytometry. Values shown are mean ±S.E. from three separate experiments with three wells/experimental condition. *P<0.001 Student's t Test.

Figure 12:
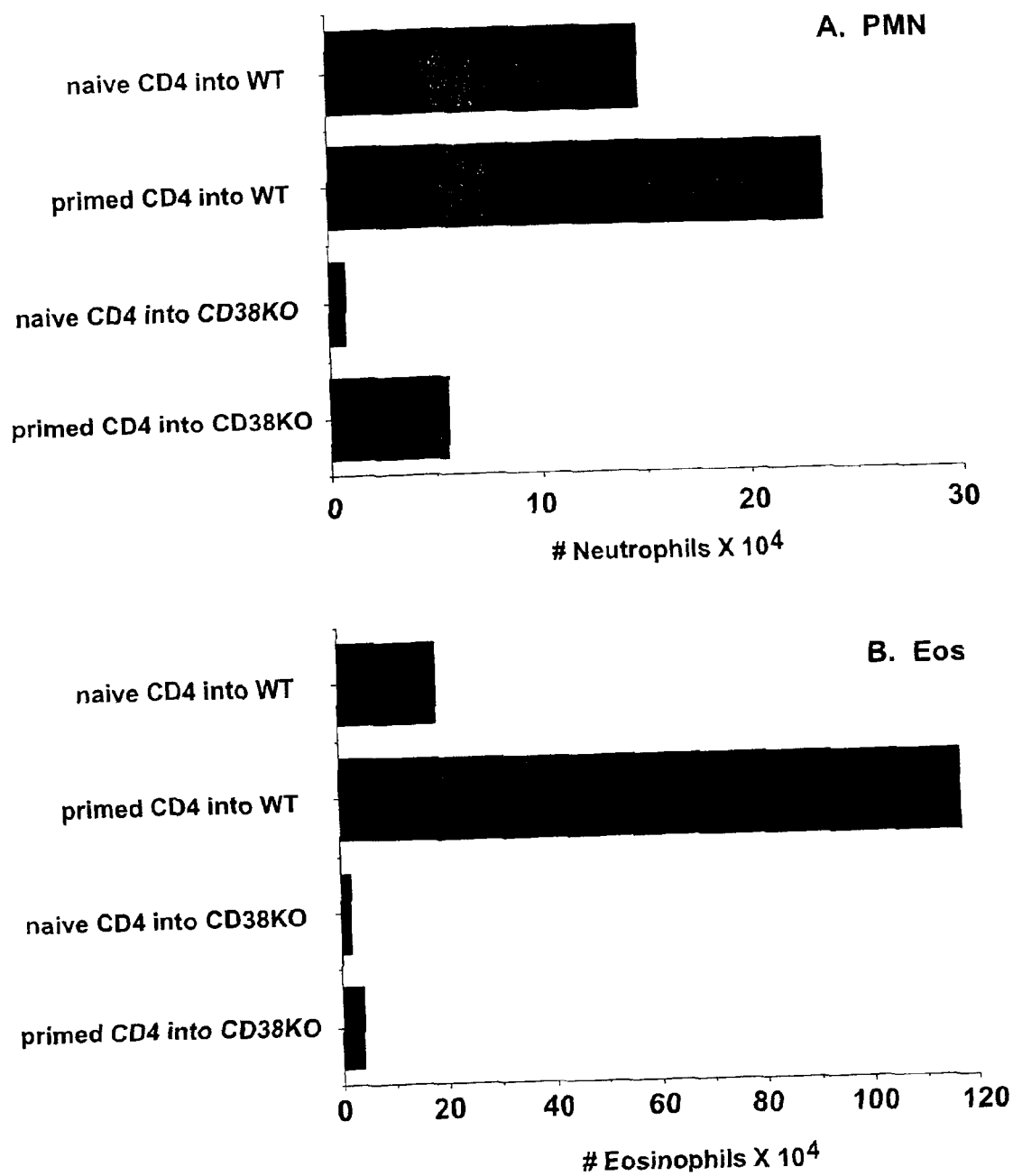

FIGS. 12A–B. The recruitment of neutrophils and eosinophils to the lungs in a model of allergic asthma is impaired in CD38 KO mice. Naive CD4 T cells from WT C57BL/6 mice or OVA-primed CD4 T cells from WT C57BL/6 mice were transferred to either WT C57BL/6 mice or to CD38KO-C57BL/6 mice as indicated. Recipient mice were subsequently challenged on 7 consecutive days by intratracheal instillation of 10 μg OVA in PBS. Neutrophils (A) and eosinophils (B) in the lung lavage on the eighth day after initial challenge were enumerated by microscopic examination (400x) of Diff-Quick stained cytocentrifuge preparations FIG. 13. Comparison of S. mansoni SM38 cDNA with S. mansoni ESTs. The SM38 cDNA (SEQ ID NO:7) was isolated and cloned from an S. mansoni cDNA library as described in methods. The cDNA for SM38 includes 5' untranslated sequence (gray box), an initiation methionine (underlined), an open reading frame encoding a 303 amino acid protein (clear box), a stop codon (underlined), 3' untranslated sequence (gray box) and a poly-adenylation site (underlined). The full-length cDNA was compared to published S. mansoni EST sequences and three separate EST sequences (SEQ ID NOS:4–6) were found that were identical to portions of the SM38 sequence. The SM38 cDNA includes 421 base pairs of unique sequence (70 bp 5' untranslated and 351 bp of open reading frame) not found in any public database.

FIG. 14. Translation of SM38 cDNA. The SM38 cDNA (SEQ ID NO:1) was translated in all reading frames and an open reading frame of 303 amino acids (SEQ ID NO:2) was identified. The initiation codon is located at nucleotide position 71–73 and the termination codon is found at nucleotide position 980–983.

FIG. 15. SM38 is homologous to Aplysia ADP-ribosyl cyclase and human CD38 cyclase. The protein sequence of SM38 (SEQ ID NO:10) was aligned with the protein sequences for Aplysia ADP-ribosyl cyclase (part a) (SEQ ID NO:8) and human ADP-ribosyl cyclase CD38 (part b) (SEQ ID NO:9). A high degree of homology (boxed residues) was observed with 21% identity between the Aplysia protein and SM38 and 23% identity between human CD38 and SM38. The conserved 10 cysteine residues present in all members of the cyclase protein family are also present in SM38 (shaded boxes). The two additional cysteines found in CD38 (underlined), but not in Aplysia, are also lacking in SM38.

However, the SM38 protein contains two additional cysteine residues that are unique and are not found in either CD38 or Aplysia cyclase (underline). Most importantly, the active site catalytic residues identified for CD38 and Aplysia enzyme (starred residues) are also present in SM38.

FIG. 16. SM38 is a soluble protein. The protein sequence of SM38 (SEQ ID NO:10) was examined to determine if the protein is a type-II membrane bound protein like CD38, a soluble protein like the Aplysia cyclase, a GPI-linked protein like other cyclase family proteins, or a secreted protein. The conserved enzyme domain (see previous figure) is shaded. SM38 contains only 22 amino acids 5' of the enzyme domain. These 22 amino acids are not hydrophobic, thus, no leader sequence 5' of the enzyme domain could be identified, indicating that SM38 is not secreted or GPI-linked. Additionally, no 5' trapsmembrane domain could be identified, indicating that SM38 is not a type-II membrane protein. Therefore, SM38 is most likely a soluble cytoplasmic protein like Aplysia cyclase.

FIG. 17. Reverse translation of SM38. The 303 amino acid coding region of SM38 was reverse-translated to identify a degenerate DNA sequence that would encode the SM38 protein (SEQ ID NO:11).

5. DETAILED DESCRIPTION OF THE INVENTION

The present invention relates to methods for modulating the migratory activity of cells involving the regulation of CD38 ADP-ribosyl cyclase activity. The invention is based on the discovery that granulocytes such as neutrophils and eosinophils from CD38KO mice cannot be efficiently recruited to sites of inflammation and infection in the body. The invention is based on the discovery that although CD38 ADP-ribosyl cyclase activity is not essential for the initial activation of granulocytes such as neutrophils, it is critically important in regulating neutrophil chemotaxis both in vivo and in vitro. In particular, cADPR, a product of CD38 ADP-ribosyl cyclase activity, is required to induce calcium release from calcium stores present within neutrophils. The release of calcium from this specialized store is necessary for activation and opening of plasma membrane channels resulting in a capacitative influx of calcium that subsequently mediates the direct migration of neutrophils toward chemoattractants and/or inflammatory products.

The present invention encompasses screening assays designed for the identification of modulators, such as agonists and antagonists, of CD38 enzyme activity and/or modulators of cADPR dependent calcium responses and chemotaxis. The invention further relates to the use of such modulators in the treatment of disorders based on the CD38 controlled migratory activity of cells to chemoattractants and inflammatory products. Such disorders include, but are not limited to, inflammation, ischemia, autoimmune disease, asthma, diabetes, arthritis, allergies, infections and organ transplant rejection.

The present invention also relates to the identification, isolation and characterization of the CD38 homologue, SM38, from the parasite S. mansoni. The invention encompasses screening assays to identify related enzymes in other pathogenic micro-organisms, such as helminths, as well as compositions and assays to screen for compounds that modulate the activity and expression of SM38. The invention further relates to the use of such modulators to treat pathogenic disorders in animals and humans infected with organisms expressing SM38 or structurally related molecules.

Various aspects of the invention are described in greater detail in the subsections below.

5.1. The SM38 Gene

The cDNA sequence (SEQ ID NO:1) and deduced amino acid sequence (SEQ ID NO:2) of S. mansoni SM38 is shown in FIG. 14 (ATCC Deposit No:). The SM38 cDNA was translated in all reading frames and an open reading frame of 303 amino acids was identified. The initiation codon is located at nucleotide position 71 and the termination codon is found at nucleotide position 981.

The SM38 nucleotide sequences of the invention include: (a) the DNA sequences shown in FIG. 14; (b) a nucleotide sequences that encodes the amino acid sequence shown in FIG. 14; (c) any nucleotide sequence that (i) hybridizes to the nucleotide sequence set forth in (a) or (b) under stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I Green Publishing Associates, Inc., and John Wiley & sons, Inc., New York, at p. 2.10.3) and (ii) encodes a functionally equivalent gene product; and (d) any nucleotide sequence that hybridizes to a DNA sequence that encodes the amino acid sequence shown in FIG. 14 under less stringent conditions, such as moderately stringent conditions, e.g., washing in 0.2×SSC/0.1% SDS at 42° C. (Ausubel et al., 1989 supra), yet which still encodes a functionally equivalent SM38 gene product. Functional equivalents of the SM38 protein include naturally occurring SM38 present in species other than S. mansoni. The invention also includes degenerate variants of sequences (a) through (d). The invention also includes nucleic acid molecules, that may encode or act as SM38 antisense molecules, useful, for example, in SM38 gene regulation (for and/or as antisense primers in amplification reactions of SM38 gene nucleic acid sequences).

In addition to the SM38 nucleotide sequences described above, homologs of the SM38 gene present in other species can be identified and readily isolated, without undue experimentation, by molecular biological techniques well known in the art. For example, cDNA libraries, or genomic DNA libraries derived from the organism of interest can be screened by hybridization using the nucleotides described herein as hybridization or amplification probes.

The invention also encompasses nucleotide sequences that encode mutant SM38s, peptide fragments of the SM38, truncated SM38, and SM38 fusion proteins. These include, but are not limited to nucleotide sequences encoding polypeptides or peptides corresponding to the cyclase domain of SM38 or portions of this domain; truncated SM38s in which the domain is deleted, e.g., a functional SM38 lacking all or a portion of the cyclase region. Certain of these truncated or mutant SM38 proteins may act as dominant-negative inhibitors of the native SM38 protein. Nucleotides encoding fusion proteins may include but are not limited to full length SM38, truncated SM38 or peptide fragments of SM38 fused to an unrelated protein or peptide such as an enzyme, fluorescent protein, luminescent protein, etc., which can be used as a marker.

SM38 nucleotide sequences may be isolated using a variety of different methods known to those skilled in the art. For example, a cDNA library constructed using RNA from cells or tissue known to express SM38 can be screened using a labeled SM38 probe. Alternatively, a genomic library may be screened to derive nucleic acid molecules encoding the SM38 protein. Further, SM38 nucleic acid sequences may be derived by performing PCR using two oligonucleotide primers designed on the basis of the SM38 nucleotide sequences disclosed herein. The template for the reaction may be cDNA obtained by reverse transcription of mRNA prepared from cell lines or tissue known to express SM38.

The invention also encompasses (a) DNA vectors that contain any of the foregoing SM38 sequences and/or their complements (e.g., antisense); (b) DNA expression vectors that contain any of the foregoing SM38 sequences operatively associated with a regulatory element that directs the expression of the SM38 coding sequences; (c) genetically engineered host cells that contain any of the foregoing SM38 sequences operatively associated with a regulatory element that directs the expression of the SM38 coding sequences in the host cell; and (d) transgenic mice or other organisms that contain any of the foregoing SM38 sequences. As used herein, regulatory elements include but are not limited to inducible and non-inducible promoters, enhancers, operators and other elements known to those skilled in the art that drive and regulate expression.

5.1.2. SM38 Proteins and Polypeptides

SM38 protein, polypeptides and peptide fragments, mutated, truncated or deleted forms of the SM38 and/or SM38 fusion proteins can be prepared for a variety of uses, including but not limited to the generation of antibodies, the identification of other cellular gene products involved in the regulation of SM38 activity, and the screening for compounds that can be used to modulate the activity of SM38.

FIG. 14 shows the deduced amino acid sequence of the SM38 protein. The SM38 amino acid sequences of the invention include the amino acid sequence shown in FIG. 14. Further, SM38s of other species are encompassed by the invention. In fact, any SM38 protein encoded by the SM38 nucleotide sequences described above is within the scope of the invention.

The invention also encompasses proteins that are functionally equivalent to the SM38 encoded by the nucleotide sequences described in Section 5.1, as judged by any of a number of criteria, including but not limited to the ability to catalyze the production of the calcium mobilizing second messenger, cADPR and thereby regulate calcium response. Such functionally equivalent SM38 proteins include but are not limited to proteins having additions or substitutions of amino acid residues within the amino acid sequence encoded by the SM38 nucleotide sequences described, above, in Section 5.1, but which result in a silent change, thus producing a functionally equivalent gene product.

Peptides corresponding to one or more domains of SM38 as well as fusion proteins in which the full length SM38, a SM38 peptide or a truncated SM38 is fused to an unrelated protein are also within the scope of the invention and can be designed on the basis of the SM38 nucleotide and SM38 amino acid sequences disclosed herein. Such fusion proteins include fusions to an enzyme, fluorescent protein, or luminescent protein which provide a marker function.

While the SM38 polypeptides and peptides can be chemically synthesized (e.g., see Creighton, 1983, Proteins: Structures and Molecular Principles, W.H. Freeman & Co., New York), large polypeptides derived from SM38 and the full length SM38 itself may be advantageously produced by recombinant DNA technology using techniques well known in the art for expressing a nucleic acid containing SM38 gene sequences and/or coding sequences. Such methods can be used to construct expression vectors containing the SM38 nucleotide sequences described in Section 5.1 and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the SM38 nucleotide sequences of the invention. Where the SM38 peptide or polypeptide is expressed as a soluble derivative and is not secreted, the peptide or polypeptide can be recovered from the host cell. Alternatively, where the SM38 peptide or polypeptide is secreted the peptide or polypeptides may be recovered from the culture media. Purification or enrichment of the SM38 from such expression systems can be accomplished using appropriate detergents and lipid micelles and methods well known to those skilled in the art. Such engineered host cells themselves may be used in situations where it is important not only to retain the structural and functional characteristics of the SM38, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing SM38 nucleotide sequences; yeast transformed with recombinant yeast expression vectors containing SM38 nucleotide sequences or mammalian cell systems harboring recombinant expression constructs containing promoters derived from the genome of mammalian cells or from mammalian viruses.

Appropriate expression systems can be chosen to ensure that the correct modification, processing and sub-cellular localization of the SM38 protein occurs. To this end, host cells which possess the ability to properly modify and process the SM38 protein are preferred. For long-term, high yield production of recombinant SM38 protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1–2 days in enriched media, and then switched to a selective media. Such engineered cell lines may be particularly useful in screening and evaluation of compounds that modulate the endogenous activity of the SM38 gene product.

5.1.3. Transgenic Animals

The SM38 gene products can also be expressed in transgenic animals. Animals of any species, including, but not limited to, mice, rats, rabbits, guinea pigs, pigs, micro-pigs, goats, and non-human primates, eg., baboons, monkeys, and chimpanzees may be used to generate SM38 transgenic animals.

Any technique known in the art may be used to introduce the SM38 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, *Proc. Natl. Acad. Sci. USA* 82:6148–6152); gene targeting in embryonic stem cells (Thompson et al., 1989, Cell, 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the SM38 transgene in all their cells, as well as animals which carry the transgene in some, but not all their cells, i.e., mosaic animals. The transgene may also be selectively introduced into and activated in a particular cell type by following, for example, the teaching of Lasko et al., (Lasko, M. et al., 1992, Proc. Natl. Acad. Sci. USA 89:6232–6236). The regulatory sequences required for such a cell-type specific activation will depend upon the particular cell type of interest, and will be apparent to those of skill in the art. When it is desired that the SM38 transgene be integrated into the chromosomal site of the endogenous SM38 gene, gene targeting is preferred. Briefly, when such a technique is to be utilized, vectors containing some nucleotide sequences homologous to the endogenous SM38 gene are designed for the purpose of integrating, via homologous recombination with chromosomal sequences, into and disrupting the function of the nucleotide sequence of the endogenous SM38 gene.

Once transgenic animals have been generated, the expression of the recombinant SM38 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of SM38 gene-expressing tissue may also be evaluated immunocytochemically using antibodies specific for the SM38 transgene product.

5.4. Antibodies to SM38 Proteins

Antibodies that specifically recognize one or more epitopes of SM38, or epitopes of conserved variants of SM38, or peptide fragments of SM38 are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in conjunction with compound screening schemes, as described, below, for the evaluation of the effect of test compounds on expression and/or activity of the SM38 gene product.

For production of antibodies, various host animals may be immunized by injection with a SM38 protein, or SM38 peptide. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacille Calmette-Guerin) and Corynebacterium parvum.

Polyclonal antibodies comprising heterogeneous populations of antibody molecules, may be derived from the sera of the immunized animals. Monoclonal antibodies may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclasses thereof. The hybridoma producing the mAb of this invention may be cultivated in vitro or in vivo. Production of high titres of Mabs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used (Morrison et al., 1984, Proc. Nat'l. Acad. Sci., 81:6851–6855; Neuberger et al., 1984, Nature, 312: 604–608; Takeda et al. 1985, Nature 314: 452–454). Alternatively, techniques developed for the production of humanized antibodies (U.S. Pat. No. 5,585, 089) or single chain antibodies (U.S. Pat. No. 4,946,778 Bird, 1988, Science 242: 423–426; Huston et al., 1988, Proc. Nat'l. Acad. Sci USA, 85: 5879–5883; and Ward et al., 1989, Nature 334: 544–546) may be used to produce antibodies that specifically recognize one or more epitopes of SM38.

5.2. Screening Assays for Compounds Useful in Modulating the Activity of CD38/SM38

The present invention relates to screening assay systems designed to identify compounds or compositions that modulate CD38/SM38 enzyme activity, cADPR mediated signal transduction, or CD38/SM38 gene expression, and thus, may be useful for modulation of cell migration or treatment of infection.

5.2.1. Recombinant Expression of CD38

For purposes of developing screening assays designed to identify compounds or compositions that modulate CD38/SM38 activity it may be necessary to recombinantly express the CD38/SM38 proteins. The cDNA sequence and deduced amino acid sequence of CD38 has been characterized from several species including human, murine and rat as described in Jackson, D. G. et al., 1990, J. Immunol. 151:3111–3118; Koguma, T. et al., 1994, Biochim Biophys Acta 1224:160–162 and Harada N et al., 1993, J Immunol 151:3111–3118, incorporated herein by reference. In addition, the cDNA and deduced amino acid sequence of Shistosoma mansoni, as described herein may be utilized to recombinantly express the CD 38 homologue, SM38, protein.

CD38/SM38 nucleotide sequences may be isolated using a variety of different methods known to those skilled in the art. For example, a cDNA library constructed using RNA from a tissue known to express CD38/SM38 can be screened using a labeled CD38/SM38 probe. Alternatively, a genomic library may be screened to derive nucleic acid molecules encoding the CD38/SM38 protein. Further, CD38/SM38 nucleic acid sequences may be derived by performing a polymerase chain reaction (PCR) using two oligonucleotide primers designed on the basis of known CD38/SM38 nucleotide sequences. The template for the reaction may be cDNA obtained by reverse transcription of mRNA prepared from cell lines or tissue known to express CD38/SM38.

CD38/SM38 protein, polypeptides and peptide fragments, mutated, truncated or deleted forms of CD38/SM38 and/or CD38/SM38 fusion proteins can be prepared for a variety of uses, including but not limited to the generation of antibodies, the identification of other cellular gene products involved in the regulation of CD38/SM38 mediated cell migration, and the screening for compounds that can be used to modulate cell migration. CD38/SM38 fusion proteins include fusions to an enzyme, fluorescent protein, a polypeptide tag or luminescent protein which provide a marker function.

While the CD38/SM38 polypeptides and peptides can be chemically synthesized (e.g., see Creighton, 1983, Proteins: Structures and Molecular Principles, W. H. Freeman & Co., New York), large polypeptides derived from CD38/SM38 and the full length CD38/SM38 itself may be advantageously produced by recombinant DNA technology using techniques well known in the art for expressing a nucleic acid containing CD38/SM38 gene sequences and/or coding sequences. Such methods can be used to construct expression vectors containing the CD38/SM38 nucleotide sequences and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the CD38/SM38 nucleotide sequences. Where the CD38/SM38 peptide or polypeptide is expressed as a soluble protein or derivative (e.g., peptides corresponding to the intracellular or extracellular domain) and is not secreted, the peptide or polypeptide can be recovered from the host cell. Alternatively, where the CD38 peptide or polypeptide is secreted the peptide or polypeptides may be recovered from the culture media. However, the expression systems also include engineered host cells that express CD38/SM38 or functional equivalents, anchored in the cell membrane. Purification or enrichment of the CD38/SM38 from such expression systems can be accomplished using appropriate detergents and lipid micelles and methods well known to those skilled in the art. Such engineered host cells themselves may be used in situations where it is important not only to retain the structural and functional characteristics of the CD38/SM38, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing CD38/SM38 nucleotide sequences; yeast transformed with recombinant yeast expression vectors containing CD38/SM38 nucleotide sequences or mammalian, helminth or insect cell systems harboring recombinant expression constructs containing promoters derived from the genome of mammalian, helminth or insect cells or from mammalian or insect viruses.

Appropriate expression systems can be chosen to ensure that the correct modification, processing and sub-cellular localization of the CD38/SM38 protein occurs. To this end, eukaryotic host cells which possess the ability to properly modify and process the CD38/SM38 protein are preferred.

For long-term, high yield production of recombinant CD38/SM38 protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1–2 days in enriched media, and then switched to a selective media. Such engineered cell lines may be particularly useful in screening and evaluation of compounds that modulate the endogenous activity of the CD38/SM38 gene products.

5.2.2. Non-cell Based Assays

In accordance with the invention, non-cell based assay systems may be used to identify compounds that interact with, i.e., bind to CD38, and regulate the enzymatic activity of CD38. Such compounds may act as antagonists or agonists of CD38 enzyme activity and maybe used to regulate cell migration including but not limited to hematopoietically derived cells. Additionally, such compounds may be used to regulate the growth, muscle contractility, differentiation, maturation and reproduction of pathogenic micro-organisms expressing SM38 or structurally related homologues. Recombinant CD38/SM38, including peptides corresponding to different functional domains or CD38/SM38 fusion proteins may be expressed and used in assays to identify compounds that interact with CD38/SM38.

To this end, soluble CD38/SM38 may be recombinantly expressed and utilized in non-cell based assays to identify compounds that bind to CD38/SM38. Recombinantly expressed CD38/SM38 polypeptides or fusion proteins containing one or more of the CD38/SM38 functional domains may be prepared as described above, and used in the non-cell based screening assays. For example, the full length CD38/SM38, or a soluble truncated CD38/SM38, e.g., in which the one or more of the cytoplasmic and transmembrane domains is deleted from the molecule, a peptide corresponding to the extracellular domain, or a fusion protein containing the CD38/SM38 extracellular domain fused to a protein or polypeptide that affords advantages in the assay system (e.g., labeling, isolation of the resulting complex, etc.) can be utilized. Where compounds that interact with the cytoplasmic domain are sought to be identified, peptides corresponding to the CD38 cytoplasmic domain and fusion proteins containing the CD38 cytoplasmic domain can be used.

The CD38/SM38 protein may also be one which has been fully or partially isolated from cell membranes or from the cytosol of cells, or which may be present as part of a crude or semi-purified extract. As a non-limiting example, the CD38 protein may be present in a preparation of cell membranes and the SM38 protein may be present in a preparation of cell cytosol. In particular embodiments of the invention, such cell membranes may be prepared using methods known to those of skill in the art.

The principle of the assays used to identify compounds that bind to CD38/SM38 involves preparing a reaction mixture of the CD38/SM38 and the test compound under conditions and for time sufficient to allow the two components to interact and bind, thus forming a complex which can be removed and/or detected in the reaction mixture. The identity of the bound test compound is then determined.

The screening assays are accomplished by any of a variety of commonly known methods. For example, one method to conduct such an assay involves anchoring the CD38/SM38 protein, polypeptide, peptide, fusion protein or the test substance onto a solid phase and detecting CD38/test compound or SM38/test compound complexes anchored on the solid phase at the end of the reaction. In one embodiment of such a method, the CD38/SM38 reactant is anchored onto a solid surface, and the test compound, which is not anchored, may be labeled, either directly or indirectly.

In practice, microtitre plates conveniently can be utilized as the solid phase. The anchored component is immobilized by non-covalent or covalent attachments. The surfaces may be prepared in advance and stored. In order to conduct the assay, the non-immobilized component is added to the coated surfaces containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the solid surface; e.g., using a labeled antibody specific for the previously non-immobilized component.

Alternatively, a reaction is conducted in a liquid phase, the reaction products separated from unreacted components using an immobilized antibody specific for CD38/SM38 protein, fusion protein or the test compound, and complexes detected using a labeled antibody specific for the other component of the possible complex to detect anchored complexes.

In accordance with the invention, non-cell based assays may also be used to screen for compounds that directly inhibit or activate enzymatic activities associated with CD38/SM38. Such activities include but are not limited to ADP-ribosyl cyclase activity, transglycosidation activity, and NAD+ glycohydrolase activity. To this end, a reaction mixture of CD38/SM38 and a test compound is prepared in the presence of substrate and the enzymatic activity of CD38/SM38 is compared to the activity observed in the absence of test compound. Substrates that may be used in the assays for detection of CD38/SM38 enzyme activity include but are not limited to NAD+ and NADP and labeled forms thereof. Additionally, derivatives of NAD such as Nicotinamide guanine dinucleotide (NGD) and Nicotinamide 1, $N^6$-etheno-adenine dinucleotide (1,N6 etheno-NAD) may be used.

In non-limiting embodiments of the invention, a reaction mixture of CD38/SM38, a test compound and substrate is prepared and the activity of CD38/SM38 is compared to the activity observed in the absence of the test compound wherein decrease in the level of CD38/SM38 enzyme activity in the presence of the test compound indicates that a CD38/SM38 antagonist has been identified. Alternatively, a reaction mixture of CD38/SM38, a test compound and substrate is prepared and the activity of CD38/SM38 is compared to the activity observed in the absence of the test compound wherein an increase in the level of CD38/SM38 enzyme activity in the presence of the test compound indicates that a CD38/SM38 agonist has been identified.

The enzymatic activity of CD38/SM38 may be detected in a variety of different ways. For example, levels of cyclic adenosine diphosphate ribose (cADPR) adenosine diphosphate ribose (ADPR) and/or nicotinic acid adenine dinucleotide phosphate (NAADP) can be measured using high performance liquid chromatography (HPLC) or thin layer chromatography (TLC) (Aarhus R et al., 1995, J. Biochem. Chem. 270:30327–30333; Muller-Steffner H M, J. Biol. Chem. 271:23967–23972; and Lund F E et al., 1999, J Immunology 162:2693–2702; Higashida, H. et al., 1997, J. Biol. Chem. 272:3127–3177) in conjunction with the use of radio-labeled substrates such as NAD or NADP or NA. Additionally, radioimmunoassays (Takahashi K et al., 1995, FEBS Lett 371:204–208; Vu C Q et al., 1997, Biochem Biophys Res Commun 236:723–726; Vu et al., Adv Exp Med Biol 419:381–388; and Graeff R M et al., 1997, Methods Enzymol 280:230–241), bioassays (Aarhus R et al., 1995, J. Biol Chem. 270:30327–30333; Clapper D L et al., J. Biol. Chem. 262:9561–9568; and Lee et al., J. Biol. Chem. 264:1608–1615) and/or fluorescent assays (Graeff R M et al., 1996, Biochem. 35:379–386; Graeff et al., 1994, J. Biol. Chem. 269:30260–30267; and Gadangi P et al., 1996, J. Immunol. 156:1937–1941) may be used for measuring cADPR, ADPR or NAADP levels. In yet another embodiment of the invention, derivatives of NAD such as NGD (Nicotinamide guanine dinucleotide) and Nicotinamide 1, $N^6$-etheno-adenine dinucleotide (1,$N^6$ etheno-NAD) may be used to measure CD38/SM38 enzyme activity. When the 1,$N^6$ etheno-NAD is hydrolysed by CD38, one of the resulting products will fluoresce (Muller et al., 1983, Biochem. J. 212:459–464; and Cockayne D et al., 1998, Blood 92:1324–1333). When the analog NGD is cyclized through the ADP-ribosyl activity of CD38/SM38 the product forms a fluorescent compound that can be detected by fluorimeter (Graeff et al., 1996, Biochem 35:379–386; and Graeff et al., 1994, J. Biol. Chem. 269:30260–30267).

In another embodiment of the invention, computer modeling and searching technologies will permit identification of potential modulators of CD38/SM38 enzyme activity. For example, based on the knowledge of the Aplysia cyclase active site (Munshi C. et al., 199, J. Biol. Chem. 274:30770–30777) and the CD38 active site (Lund F E et al., 1999, J. Immunology 162:2693–2702; Munshi, C et al., 2000, J. Biol. Chem. 275:21566–21571; Graeff R et al., 2001, J. Biol. Chem. 276:12169–12173) and the study of complexes between CD38/SM38 substrates and substrate anologs, potential modulators of CD38/SM38 activity may be identified.

The three dimensional geometric structure of the active site may be determined using known methods, including x-ray crystallography, which can determine a complete molecular structure (see, for example, Prasad G S et al., Nature Struc. Biol. 3:957–964 which describes the crystal structure of Aplysia ADP ribosyl cyclase). On the other hand, solid or liquid phase NMR can be used to determine certain intramolecular distances. Any other experimental method of structure determination can be used to obtain the partial or complete geometric structure of the CD38 active site.

Having determined the structure of the CD38/SM38 active site, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential CD38 modulating compounds.

Alternatively, these methods can be used to identify improved modulating compounds from an already known modulating compounds. For example, a number of compounds that modulate the enzyme activity of other enzymes that utilize NAD/NADP as substrates (i.e., PARP family homologues) have already been identified. The composition of the known compound can be modified and the structural effects of modification can be determined using experimental and computer modeling methods applied to the new composition. The altered structure is then compared to the active site structure of the compound to determine if an improved fit or interaction results. In this manner systematic variations in composition, such as by varying side groups, can be quickly evaluated to obtain modified modulating compounds or substrates of improved specificity or activity.

5.2.3. Cell Based Assays

In accordance with the invention, a cell based assay system can be used to screen for compounds that modulate the activity of CD38/SM38. In accordance with the invention, a cell-based assay system can be used to screen for compounds that modulate the activity of CD38 and thereby, modulate the chemoattractant induced $Ca^{2+}$ influx and the migration of cells. Additionally, this cell based system can be used to screen for compounds that modulate the activity of SM38, and thereby, modulate intracellular calcium release and/or muscle contractility in cells. To this end, cells that endogenously express CD38/SM38 can be used to screen for compounds. Such cells include, for example, neutrophils, lymphocytes, eosinophils, macrophages and dendritic cells. In addition, S. mansoni cells that express SM38, may be used to screen for compounds. Alternatively, cell lines, such as 293 cells, COS cells, CHO cells, fibroblasts, and the like, genetically engineered to express CD38/SM38 can be used for screening purposes. For screens utilizing host cells genetically engineered to express a functional CD38 protein, it would be preferred to use host cells that are capable of responding to chemoattractants or inflammatory stimuli. For screens utilizing host cells genetically engineered to express SM38, it would be preferable to use cells of S. mansoni origin that are capable of responding to a variety fo stimuli such as acetylcholine or high concentrations of K+ to induce muscle contraction. Further, ooyctes or liposomes engineered to express the CD38/SM38 protein may be used in assays developed to identify modulators of CD38/SM38 activity.

The present invention provides methods for identifying compounds that alter one of more of the enzymatic activities of CD38/SM38, including but not limited to, NAD glycohydrolase activity, ADP-ribosyl cyclase activity and/or transglycosidation (exchange) activity. Specifically, compounds may be identified that promote CD38/SM38 enzyme activities, i.e., agonists, or compounds that inhibit CD38/SM38 enzyme activities, i.e., antagonists. Compounds that inhibit CD38 enzyme activities will be inhibitory for chemoattractant induced calcium responses and cell migration (FIG. 2). Compounds that activate CD38 enzyme activity will enhance chemoattractant induced calcium responses and cell migration. Compounds that either activate or inhibit SM38 enzyme activities will alter the viability or functional activities of pathogenic organisms expressing SM38. Such compounds maybe compounds that interact with the active site of CD38/SM38 thereby modulating enzyme activity, or compounds that compete/facilitate substrate binding to CD38/SM38 or compete/inhibit catalysis of substrate (FIG. 2). Alternatively, compounds may be identified that modulate the activity of proteins that modify the CD38/SM38 protein, i.e., phosphorylate, ribosylate, etc., and thereby regulate the activity of CD38 (FIG. 3). Such proteins include for example, ADP-ribosyl transferases which ribosylate CD38/SM38 and render CD38/SM38 enzymatically inactive. In addition, compounds may be identified that regulate CD38/SM38 expression and thereby regulate the level of enzyme activity within a cell (FIG. 4).

The present invention provides for methods for identifying a compound that activates CD38/SM38 enzyme activity comprising (i) contacting a cell expressing CD38/SM38 and chemoattractant receptors with a test compound in the presence of substrate and measuring the level of CD38/SM38 activity; (ii) in a separate experiment, contacting a cell expressing CD38/SM38 protein and chemoattractant receptors with a vehicle control in the presence of substrate and measuring the level of CD38/SM38 activity where the conditions are essentially the same as in part (i), and then (iii) comparing the level of CD38/SM38 activity measured in part (i) with the level of CD38/SM38 activity in part (ii), wherein an increased level of CD38/SM38 activity in the presence of the test compound indicates that the test compound is a CD38/SM38 activator.

The present invention also provides for methods for identifying a compound that inhibits CD38/SM38 enzyme activity comprising (i) contacting a cell expressing CD38/SM38 and chemoattractant receptors with a test compound in the presence of a chemoattractant and substrate and measuring the level of CD38/SM38 activity; (ii) in a separate experiment, contacting a cell expressing CD38/SM38 and chemoattractant receptors with a chemoattractant and substrate and measuring the level of CD38/SM38 activity, where the conditions are essentially the same as in part (i) and then (iii) comparing the level of CD38/SM38 activity measured in part (i) with the level of CD38/SM38 activity in part (ii), wherein a decrease level of CD38/SM38 activity in the presence of the test compound indicates that the test compound is a CD38/SM38 inhibitor.

Depending on the assays used to detect CD38/SM38 activity, the methods described above for identifying activators and inhibitors of CD38/SM38 may include the presence or absence of a chemoattractant in steps (i) and (ii). For example, when assaying directly for CD38/SM38 ADP-ribosyl cyclase activity or the production of CD38/SM38 metabolites, the presence of a chemoattractant or the expression of a chemoattractiant receptor on the test cell may not be required. However, in instances where, for example, chemotaxis or changes in intracellular calcium levels are measured in CD-38-expressing cells it may be necessary to include chemoattractants. Alternatively, when muscle contractility or changes in intracellular calcium levels are measured in SM38-expressing cells, it may be necessary to include stimulants to activate muscle contraction and/or calcium release including, but not limited to, acetylcholine, serotonin (Day et al., 1994, Paristol. 108:425–432), FMRF-amide related peptides (FaRPs) (Day et al., 1994, Paristol. 109:455–459) or high K+ concentrations in the media (Day et al., 1993, Paristol. 106:471–477). Additionally, it will be necessary to perform these experiments with host cells that express the receptors specific for the stimulants utilized. Those skilled in the art will be able to determine operative and optimal assay conditions by employing routine experimentation.

A "chemoattractant", as defined herein, is a compound or molecular complex that induces the migration of cells via a mechanism that is dependent on the production of cADPR by CD38. An example of such a chemoattractant includes, but is not limited to, fMet-leu-Phe (fMLP). Other chemoattractants that may be used include, eotaxin, GRO-1, IP-10, SDF-1, BLC, Rantes, MIP-1A, MCP-3, MIP3a, IL-8, CLS, ELC, Lymphotactin, PAF, Ltb4, complement c5a and histamine.

In utilizing the cell systems described above, such cell systems, the cells expressing the CD38/SM38 protein are exposed to a test compound or to vehicle controls (e.g., placebos). After exposure, the cells can be assayed to measure the activity of CD38/SM38 or the activity of the CD38 dependent signal transduction pathway itself can be assayed.

The ability of a test molecule to modulate the activity of CD38/SM38 may be measured using standard biochemical and physiological techniques. Responses such as activation or suppression of CD38/SM38 ADP-ribosyl cyclase activity or the production of CD38/SM38 metabolites such as cADPR and/or NAADP can be measured. Levels of cADPR, ADPR and/or NAADP can be measured using HPLC or TLC in conjunction with the use of radio-labeled substrates such as NAD or NADP or NA. Additionally, radioimmunoassays, bioassays and/or fluorescent assays, such as those discussed in Section 5.1.1, supra, may be used for measuring cADPR or NAADP levels. In yet another embodiment of the invention, derivatives of NAD such as NGD (Nicotinamide guanine dinucleotide) and Nicotinamide 1, $N^6$-etheno-adenine dinucleotide (1,$N^6$ etheno-NAD) may be used to measure CD38/SM38 activity.

Test compounds may also be assayed utilizing cell based calcium and/or migration assays to identify compounds that are capable of inhibiting or activating chemoattractant induced CD38 dependent calcium responses and cell migration. In non-limiting embodiments of the invention, changes in intracellular $Ca^{2+}$ levels may be monitored by the fluorescence of $Ca^{2+}$ indicator dyes such as Indo, Fluo-3 and Fura-Red, etc. Further, changes in membrane potential resulting from modulation of the CD38/SM38 enzyme activity can be measured using a voltage clamp or patch recording methods. Directed migration of cells may also be monitored by standard chemotaxis assays in modified Boyden chambers or on slides. Such assay systems are described in further detail in the working example of the present specification (See, Example 6). Muscle contractility may also be measured by standard assays described in detail in the literature (for example: (Day et al., 1994 *Parasitology* 109:455–9) and references therein).

After exposure to the test compound, or in the presence of a test compound, cells can be stimulated with a chemoattractant such as fMLP or a muscle activator such as high K+ concentrations, and changes in intracellular calcium levels, cADPR or NAADP levels, muscle contractility and/or cell migration may be measured. These measurements will be compared to cells treated with the vehicle control. Increased levels of intracellular $Ca^{2+}$, increased production of cADPR, increases in muscle contractility and/or increased migration of cells toward a chemoattractant in the presence of a test compound indicates that the compound acts as an agonists to increase the Ca2+ response increase muscle contractility and increase chemoattractant induced CD38 dependent cell migration. Decreased levels of intracellular Ca2+, decreased production of cADPR, decreased muscle contractility and/or decreased migration of cells toward a chemoattractant in the presence of a test compound indicates that the compound acts as an antagonist and inhibits the Ca2+ response, decreases muscle contractility and inhibits chemoattractant induced CD38 dependent cell migration (see, for example, FIGS. 2 and 3).

In addition, the assays of the invention may be used to identify compounds that (i) function as substrates of CD38/SM38 enzymatic activity and are converted into agonists or antagonists of cADPR dependent Ca2+ signal transduction pathway (FIG. 5). A compond fitting these specifications is described in further detail in the working exmaple of the present specification (Example 6, FIG. 11). Alternatively, the assays of the invention may be used (ii) to identify compounds that specifically interfere with the cADPR mediated Ca2+ signal transduction pathways (FIG. 6). In a non-limiting embodiment of the invention, test compounds may include chemical derivatives of any known and unknown substrates of CD38/SM38 (for example, the substrate analog 8-Br-βNAD is converted into the modified product 8-Br-cADPR which acts as an antagonist of cADPR mediated Ca2+ signal transduction). The test substrate may be administered to cells expressing CD38/SM38 and the appropriate chemoattractant receptors in the presence of the chemoattractant or muscle stimulant. Conversion of the modified test substrate into a modified product that is capable of modulating the activity of cADPR can be measured utilizing the methods described above. Test substrates may also be assayed to determine their effect on calcium influx, muscle contractility and/or cell migration. Intracellular Ca2+ accumulation and directed migration to a chemoattractant can be measured in cells treated with the test substrate and the chemoattractant and compared to cells receiving the non-modified substrate. i.e., NAD and a chemoattractant. Compounds which are converted into modified products, i.e., 8-Br-cADPR, and competitively or non-competitively inhibit cADPR induced calcium responses, muscle contractility or directed migration will be identified as antagonists of the cADPR $Ca^{2+}$ signaling pathway, while compounds that are converted into modified products that are competitive or non-competitive agonists of the cADPR $Ca^{2+}$ signaling pathway will be defined as agonists or activators.

In yet another embodiment of the invention, compounds that directly alter (i.e., activate or inactivate) the activity of cADPR, i.e., induced calcium release and cell migration, can be tested in assays. Such agonists or antagonists would be expected to modulate the influx of Ca2+ into the cell resulting in changes in the cell's migratory activity or ability to contract. Antagonists would have reduced Ca2+ responses, reduced contractility and/or reduced migration in the presence of a chemoattractant. Examples of antagonists include, but are not limited to 8-NH$_2$-cADPR, 8-Br-cADPR, 8-CH$_3$-cADPR, 8-OCH$_3$-cADPR and 7-Deaza-8-Br-cADPR. A compound fitting these specifications is described in further detail in the working example of the present specification (Example 6, FIG. 10).Agonists would have increased Ca2+ responses, increased contractility and/or increased migration in the presence of chemoattractants. Examples of agonists include but are not limited to 2'-deoxy-cADPR, 3'-deoxy-cADPR and 2'-phospho-cADPR. Assays for direct measurement of cAPDR activity include the bioassays such as those described by Howard et al. (1995, Science 262:1056); Galione et al. (1993, *Nature* 365:456–459) and Lee and Aarhus (1991, Cell Regulation 2:203–209).

Further, the assays of invention may identify compounds that are capable of activating CD38/SM38 enzyme activity, i. e., agonists, but which desensitize the calcium pathway by depletion of intracellular calcium stores. Such desensitization may, in some instances, lead to inhibition of cell migration or muscle contraction due to the depletion of calcium stores. Thus compounds may be identified that function as agonists in CD38/SM38 enzyme assays but function as antagonists in chemotaxis or muscle contraction assays. Such assays and compounds are within the scope of the present invention.

5.2.4. Assay for Compounds that Regulate the Expression of CD38/SM38

In accordance with the invention, a cell based assay system can be used to screen for compounds that modulate the expression of CD38/SM38 within a cell. Assays may be designed to screen for compounds that regulate CD38/SM38 expression at either the transcriptional or translational level. In one embodiment, DNA encoding a reporter molecule can be linked to a regulatory element of the CD38/SM38 gene and used in appropriate intact cells, cell extracts or lysates to identify compounds that modulate CD38/SM38 gene expression. Such reporter genes may include but are not limited to chloramphenicol acetyltransferase (CAT), luciferase, β-glucuronidase (GUS), growth hormone, or placental alkaline phosphatase (SEAP). Such constructs are introduced into cells thereby providing a recombinant cell useful for screening assays designed to identify modulators of CD38/SM38 gene expression.

Following exposure of the cells to the test compound, the level of reporter gene expression may be quantitated to determine the test compound's ability to regulate CD38/SM38 expression. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemiluminescent assays such as those described in Bronstein, I. et al. (1994, *Biotechniques* 17: 172–177). Such assays provide a simple, sensitive easily automatable detection system for pharmaceutical screening.

To identify compounds that regulate CD38/SM38 translation, cells or in vitro cell lysates containing CD38/SM38 transcripts may be tested for modulation of CD38/SM38 mRNA translation. To assay for inhibitors of CD38/SM38 translation, test compounds are assayed for their ability to modulate the translation of CD38/SM38 mRNA in in vitro translation extracts.

In an embodiment of the invention, the level of CD38/SM38 expression can be modulated using antisense or ribozyme approaches to inhibit or prevent translation of CD38/SM38 mRNA transcripts or triple helix approaches to inhibit transcription of the CD38/SM38 gene. Such approaches may be utilized to treat disorders such as inflamation and allergies where inhibition of CD38/SM38 expression is designed to prevent hematopoietically-derived cell migration or inhibition of SM38 is designed to alter *S. mansoni* physiology and pathogenesis.

Antisense approaches involve the design of oligonucleotides (either DNA or RNA) that are complementary to CD38/SM38 mRNA. The antisense oligonucleotides will bind to the complementary mRNA transcripts and prevent translation. Absolute complementarity, although preferred, is not required. One skilled in the art can ascertain a tolerable degree of mismatch by use of standard procedures to determine the melting point of the hybridized complex.

In yet another embodiment of the invention, ribozyme molecules designed to catalytically cleave CD38/SM38 mRNA transcripts can also be used to prevent translation of CD38/SM38 mRNA and expression of CD38/SM38. (See, e.g., PCT International Publication WO90/11364, published Oct. 4, 1990; Sarver et al., 1990, Science 247:1222–1225). Alternatively, endogenous CD38/SM38 gene expression can be reduced by targeting deoxyribonucleotide sequences complementary to the regulatory region of the CD38/SM38 gene (i.e., the CD38 promoter and or enhancers) to form triple helical structures that prevent transcription of the CD38/SM38 gene in targeted hematopoietically-derived cells in the body. (See generally, Helene, C. et al., 1991, Anticancer Drug Des. 6:569–584 and Maher, L J, 1992, Bioassays 14:807–815).

The oligonucleotides of the invention, i.e., antisense, ribozyme and triple helix forming oligonucleotides, may be synthesized by standard methods known in the art, e.g., by use of an automated DNA synthesizer (such as are commercially available from Biosearch, Applied Biosystems, etc.). Alternatively, recombinant expression vectors may be constructed to direct the expression of the oligonucleotides of the invention. Such vectors can be constructed by recombinant DNA technology methods standard in the art. In a specific embodiment, vectors such as viral vectors may be designed for gene therapy applications where the goal is in vivo expression of inhibitory oligonucleotides in targeted cells.

5.2.5. Compounds that can be Screened in Accordance with the Invention

The assays described above can identify compounds which modulate CD38/SM38 activity. For example, compounds that affect CD38/SM38 activity include but are not limited to compounds that bind to CD38/SM38, and either activate enzyme activities (agonists) or block enzyme activities (antagonists). Alternatively, compounds may be identified that do not bind directly to CD38/SM38 but are capable of altering CD38/SM38 enzyme activity by altering the activity of a protein that regulates CD38 enzyme activity (see, FIG. 3) Compounds that are substrates of CD38 that are converted into modified products that activate or inhibit the cADPR Ca2+ signal transduction pathway can also be identified by the screens of the invention. Compounds that directly activate or inhibit the cADPR Ca2+ signal transduction pathway in cells can also be identified. Additionally, compounds that activate CD38/SM38 enzyme activity resulting in desensitization of the calcium pathway may be identified. Such desensitizing compounds would be expected to inhibit cell migration. Further, compounds that affect CD38/SM38 gene activity (by affecting CD38/SM38 gene expression, including molecules, eg., proteins or small organic molecules, that affect transcription or interfere with splicing events so that expression of the full length or the truncated form of the CD38/SM38 can be modulated) can be identified using the screens of the invention.

The compounds which may be screened in accordance with the invention include, but are not limited to, small organic or inorganic compounds, peptides, antibodies and fragments thereof, and other organic compounds (e., peptidomimetics) that bind to CD38/SM38 and either mimic the activity triggered by any of the known or unknown substrates of CD38/SM38 (i.e., agonists) or inhibit the activity triggered by any of the known or unknown substrates of CD38/SM38 (i.e., antagonists). Compounds that bind to CD38/SM38 and either enhance CD38/SM38 enzyme activities (i.e., ADP-ribosyl cyclase activity, NAD glycohydrolase activity, transglycosidation activity), i.e., agonists, or compounds that inhibit CD38/SM38 enzyme activities, i.e., antagonists, in the presence or absence of the chemoattractant or muscle stimulant will be identified. Compounds that bind to proteins that alter/modulate the enzyme activity of CD38/SM38 will be identified. Compounds that mimic natural substrates, i.e., NAD(P) and are converted by CD38/SM38 enzyme activities into products that act as agonists or antagonists of the cADPR induced calcium release pathway can be identified. Compounds that directly activate or inhibit the cADPR Ca2+ signal transduction pathway in cells can be identified.

Compounds may include, but are not limited to, peptides such as, for example, soluble peptides, including but not limited to members of random peptide libraries (see, e.g., Lam, K. S. et al., 1991, Nature 354:82–84; Houghten, R. et al., 1991, Nature 354:84–86); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope binding fragments thereof, and small organic or inorganic molecules.

Other compounds which may be screened in accordance with the invention include but are not limited to small organic molecules that affect the expression of the CD38/SM38 gene or some other gene involved in the CD38/SM38 signal transduction pathway (e., by interacting with the regulatory region or transcription factors involved in gene expression); or such compounds that affect the enzyme activities of the CD38/SM38 or the activity of some other factor involved in modulating CD38/SM38 enzyme activity, such as for example, a protein that ribosylates CD38/SM38 and thereby inactivates CD38/SM38 enzyme activities.

5.3. Compositions Containing Modulators of CD38/SM38 and their Uses

The present invention provides for methods of modulating cell migration comprising contacting a cell expressing CD38 with an effective amount of a CD38 modulating compound, such as a CD38 agonist or antagonist identified using the assays as set forth in Section 5.1 supra. Additionally, the present invention provides for methods of modulating calcium responses and/or muscle contractility comprising contacting a cell expressing SM38 with an effective amount of a SM38 modulating compound, such as a SM38 agonist or antagonist identified using the assays as set forth in Section 5.1 supra. An "effective amount" of the CD38/SM38 inhibitor, i.e., antagonist, is an amount that decreases chemoattractant induced cell migration decreases intracellular calcium levels, decreases muscle contraction and/or that is associated with a detectable decrease in CD38/SM38 enzyme activity as measured by one of the above assays. An "effective amount" of the CD38/SM38 activator, i.e., agonist, is an amount that subjectively increases chemoattractant induced cell migration, increases intracellular calcium levels, increases muscle contraction and/or that is associated with a detectable increase in CD38/SM38 enzyme activity as measured by one of the above assays. Compositions of the invention also include modified CD38/SM38 substrates, modulators of CD38/SM38 expression and agonists/antagonists of cADPR.

The present invention further provides methods of modulating cell migration in a subject, comprising administering to the subject, a composition comprising a compound that modulates CD38 enzyme activity identified as set forth in Section 5.1 supra. The composition may comprise an amount of CD38 enzyme activator or inhibitor, modulators of CD38 expression, modified CD38 substrates, or direct agonists/antagonists of cADPR controlled Ca2+ responses. Accordingly, the present invention provides for compositions comprising CD38 activators and inhibitors.

The present invention provides for compositions comprising an effective amount of a compound capable of modulating the activity of CD38, the expression of CD38 and/or the activity of cADPR thereby regulating the migratory activity of cells, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The invention provides for treatment or prevention of various diseases and disorders associated with cell migration by administration of a compound that regulates the expression or activity of CD38. Such compounds include but are not limited to CD38 antibodies; CD38 antisense nucleic acids, CD38 agonists and antagonists (see, FIGS. 2–3), modified CD38 substrates (see, FIG. 5) and cADPR agonists and antagonists (see, FIG. 6). In a non-limiting embodiment of the invention, disorders associated with hematopoietic derived cell migration are treated or prevented by administration of a compound that regulates CD38 activity. Such disorders include but are not limited to inflammation, ischemia, asthma, auto-immune disease, diabetes, allergies, infections, arthritis and organ transplant rejections.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing CD38 are exposed to or otherwise administered a therapeutic compound and the effect of such a therapeutic upon CD38 activity is observed. In a specific embodiment of the invention the ability of a compound to regulate, i.e., activate or inhibit cell migration may be assayed.

The present invention further provides methods of modulating the muscle contraction or other physiologic parameters in helminths such as S. mansoni by administering to helminth infected subject, a composition comprising a compound that modulates SM38 enzyme activity identified as set forth in Section 5.1 supra. The composition may comprise an amount of SM38 enzyme activator or inhibitor, modulators of SM38 expression, modified SM38 substrates, or direct agonists/antagonists of cADPR controlled Ca2+ responses. Accordingly, the present invention provides for compositions comprising SM38 activators and inhibitors.

The present invention provides for compositions comprising an effective amount of a compound capable of modulating the activity of SM38, the expression of SM38 and/or the activity of cADPR thereby regulating the activity and viability of the parasite, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

The invention provides for treatment or prevention of various diseases and disorders associated with helminth infections. Such compounds include but are not limited to SM38 antibodies; SM38 antisense nucleic acids, SM38 agonists and antagonists (see, FIGS. 2–3), modified SM38 substrates (see, FIG. 5) and cADPR agonists and antagonists (see, FIG. 6). In a non-limiting embodiment of the invention, disorders associated with helminth infection are treated or prevented by administration of a compound that regulates SM38 activity. Such disorders include but are not limited to granuloma formation and fibrosis in the liver and lung.

The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing SM38 are exposed to or otherwise administered a therapeutic compound and the effect of such a therapeutic upon SM38 activity is observed. In a specific embodiment of the invention the ability of a compound to regulate, i.e., activate or inhibit muscle contractility or intracellular calcium accumulation. Additionally, the compounds of the invention may be assayed for their effect on S. mansoni pathogenesis, growth, differentiation, and reproduction in a mouse model for S. mansoni infection. Such assays would include the testing for effects on proliferation of parasites, maturation of female worms, quantity of granulomas in liver and lung, quantity of eggs in liver, lung bladder and intestines, quantity of worms in lung and liver and quantity of miracidia detected in urine and feces.

Additionally, the compounds of the invention may be assayed for their effect on S. mansoni pathogenesis, growth, differentiation, and reproduction. Such compounds could be tested in a mouse model for S. mansoni infection. Such assays would include the testing for effects on proliferation of parasites, quantity of granulomas in liver and lung, quantity of eggs in liver, lung bladder and intestines and quantity of miracidia detected in urine and feces.

The invention provides methods of treatment and/or prophylaxis by administration to a subject of an effective amount of a compound of the invention. In a preferred aspect, the compound is substantially purified. The subject is preferably an animal, and is preferably a mammal, and most preferably human.

Various delivery systems are known and can be used to administer a compound capable of regulating CD38 activity, cADPR, or CD38 expression, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429–4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The present invention also provides pharmaceutical compositions. Such compositions comprise a therapeutically effective amount of a compound capable of regulating CD38 activity, cADPR activity or CD38 expression and a pharmaceutically acceptable carrier. In a specific embodiment, the term "pharmaceutically acceptable" means approved by a regulatory agency of the Federal or a state government or listed in the U.S. Pharmacopeia or other Generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE

Neutrophils Require CD38 for Chemotaxis, Capacitative Ca+ Entry and Bacterial Clearance The subsection below describes data demonstrating that calcium entry in chemoattractant activated neutrophils is controlled by cADPR, a product of the CD38 enzyme reaction. The capacitative calcium influx, controlled by the cADPR produced by CD38, is required for neutrophils to migrate efficiently to chemoattractants.

6.1. Material and Methods

6.1.1. Mice

C57BL/6J x 129 CD38KO F2 animals(Cockayne et al., 1998 *Blood* 92:1324–1333) backcrossed 6 generations (N6)

to C57BL/6J and then inbred to produce homozygous congenic C57BL/6J.129 CD38KO mice. CD38-Rag-2 double KO (dKO) mice were produced by crossing C57BL/6J.129 (N6) CD38KO mice with C57BL/6J.129 (N8) Rag-2 KO mice (Shin Kai et al., 1992 *Cell* 68:855–867) and then mating the offspring to obtain homozygous double KO animals. Bone marrow chimeric mice were produced by transplanting $1\times10^7$ whole bone marrow cells isolated from WT or CD38KO mice into lethally irradiated (950 rad) WT hosts. All mice were bred and maintained in the Trudeau Institute Animal Breeding Facility.

6.1.2. cADPR Content Measurements

Mouse tissues were isolated from whole-body perfused WT or CD38KO mice and were flash frozen in liquid nitrogen. Bone marrow myeloid cells were flushed from the tibias and femurs of Rag-2KO or Rag-2-CD38 dKO mice. cADPR content in mouse tissues and bone marrow myeloid cells was then measured as previously described (Vu et al., 1997 *Biochem Biophys Res Commun* 236:723–726).

S. pneumoniae infection. Mice were infected intratracheally with 100 or 1000 CFU *S. pneumoniae* type 4 (Klein Strain) from American Type Tissue Culture (Rockville, Md.). Blood, bronchial-aveolar lavage fluid (BAL) and lung tissue were collected from infected mice (Garvy et al., 1996 *Inflammation* 20:499–512). Bacterial titers in lung homogenate and blood were calculated on a per lung basis or per ml of blood. BAL cells were enumerated from cyto-centrifuge preparations.

6.1.3. In Vitro Chemotaxis Assays

Bone marrow neutrophils were purified (95% purity) by positive selection using biotinylated GR-1 (PharMingen) and MACS Streptavidin Microbeads (Miltenyi Biotec, Auburn Calif.). Chemotaxis assays(Falk et al., 1980 *J. Immuno. Methods* 33:239–247) were performed using 24-well transwell plates with a 3 μm pore size polycarbonate filter (Costar, Cambridge, Mass.). Medium (HBSS+Ca2$^+$+Mg2$^+$), fMLP (1 μM, Sigma, St. Louis, Mo.), or IL-8 (100 nM, Sigma) was placed in the lower and/or upper chamber in a checkerboard format.$1\times10^5$ neutrophils were loaded in the upper chamber and the plates were incubated at 37° C. for 45 min. The transmigrated cells were collected from the lower chamber, fixed and counted on the flow cytometer (FACS Calibur, Becton Dickinson, San Jose Calif.). To determine the absolute number of cells in each sample, a standard number of 20 μM size fluorescent microspheres (Polysciences, Inc. Warrington, Pa.) was added to each tube and counted along with the cells. The total number of transmigrated cells=the number of counted neutrophils X total number of beads/beads counted. In some experiments, neutrophils were incubated in EGTA (2 mM) or pre-treated for 20 min with 8-Br-cADPR (25–100 μM, Sigma) or N(8-Br-A)D+(1.0 mM).

6.1.4. CD38 Expression

Bone marrow, blood or peritoneal cavity cells were isolated from WT or CD38KO mice and stained with anti-mouse GR-1 FITC, anti-mouse MAC-1 PE and anti-mouse CD38 APC (PharMingen, San Diego Calif.). Human peripheral blood neutrophils were isolated on a ficoll gradient and then stained with anti-hCD15-FITC (Becton Dickinson, San Jose Calif.) and anti-hCD38-Biotin (Caltag Laboratories, Burlingame Calif.). Mouse and human neutrophils were analyzed by flow cytometry, gating on the MAC-1$^+$GR-1$^+$ for mouse neutrophils and CD15+ for human neutrophils. To induce an inflammatory response, mice were injected with 1 ml 3% thioglycollate medium intra-peritoneally (Becton Dickinson, Cockeysville Md.). The animals were sacrificed 12 hrs post-injection, and the cells infiltrating the peritoneal cavity were collected.

6.1.4. Measurement of CD38 Cyclase Activity

Measurement of CD38 cyclase activity. $1\times10^6$ purified bone marrow neutrophils were incubated for 20 min at 37° C. in 100 μl HBSS in a 96 well microplate. NGD (40 μM) (Sigma) was added and the enzymatic conversion of NGD$^+$ to cGDPR was measured fluorometrically (Graeff et al., 1994 *J. Biol. Chem.* 269:30260–30267) over the next 10 minutes (415 nm emission and 300 nm excitation).

6.1.5. RYR-3 mRNA Expression in Neutrophils cDNA was prepared from RNA isolated from purified bone marrow neutrophils or brain tissue. 30 cycles (annealing temperature 61° C.) RT-PCR was performed with 0.03–2 μg input cDNA and RyR-3 specific primers (Guse et al., 1999 *Nature* 398:70–73).

Synthesis of N(8-Br-A)D$^+$. N(8-Br-A)D$^+$ was synthesized as previously described (Abdallah et al. 1975 *Eur. J Biochem* 50:475–481).

6.1.6. Intracellular Calcium Measurements

Purified bone marrow neutrophils were resuspended in cell loading media (HBSS with Ca2$^+$ and Mg2$^+$+1% FBS+4 mM probenecid) at $1\times10^7$ cells/ml. The cells were incubated at 37° C. for 30 min with the fluorescent dyes Fluo-3 AM (4 μg/ml) and Fura Red AM (10 μg/ml) (Molecular Probes, Eugene Oreg.) and then washed twice and resuspended in cell loading medium or calcium-free medium at $1\times10^6$ cells/ml. In some experiments, cells were permeabilized with 5 μM digitonin in calcium-free media. In other experiments, cells were preincubated with EGTA (2 mM), 8-Br-cADPR (10–100 μM), ruthenium red (Sigma) or N(8-Br-A)D$^+$ (1 mM) and then stimulated with the carrier control (DMSO 0.01%), fMLP (1 μM), IL-8 (100 nM), ryanodine (1 μM), cADPR (100 μM) or thapsigargin (1 μm). The accumulation of [Ca$^{2+}$]i in individual cells was assessed by flow cytometry measuring the fluorescence emission of Fluo-3 in the FL-1 channel and Fura-Red in the FL-3 channel. Data was analyzed using FlowJo 3.2 (Tree Star, Inc. San Carlos, Calif.). The relative [Ca2$^+$]i was expressed as the ratio between Fluo-3 and Fura Red mean fluorescence intensity over time.

6.2. Results

CD38 is the primary ADP-ribosyl cyclase expressed in lymphoid tissues. To directly test the requirement for CD38 and cADPR in calcium-sensitive immunologic responses in vivo, CD38 knockout (CD38KO) mice where generated (Cockkayne et al. 1998 *Blood* 92:1324–1333). To determine whether CD38 is the primary cyclase expressed in mice, the cADPR content in tissues and cells isolated from CD38KO and C57BL/6J wild-type (WT) mice were compared(Table 1).

TABLE 1

Comparison of cADPR content in tissues isolated from CD38KO and WT animals.

| Tissue | cADPR content WT tissue (pmol/mg protein) | cADPR content CD38KO tissue (pmol/mg protein) |
| --- | --- | --- |
| Spleen | 2.108 ± 0.334 | 0.298 ± 0.091* |
| Thymus | 0.769 ± 0.182 | 0.335 ± 0.088** |
| BM myeloid | 0.633 ± 0.111 | 0.257 ± 0.032* |
| Lung | 0.847 ± 0.213 | 0.480 ± 0.069 |
| Kidney | 0.488 ± 0.119 | 0.418 ± 0.070 |
| Heart | 1.249 ± 0.324 | 1.014 ± 0.237 |
| Brain | 3.865 ± 0.866 | 3.127 ± 0.316 |

Extracts were prepared from tissues isolated from 8–12 wk old CD38KO or WT mice or from bone marrow (BM) myeloid cells isolated from Rag-2KO or Rag-2-CD38 double KO mice and were analyzed for cADPR content. Three separate purifications and analyses were performed on tissues isolated from 3 mice/analysis. *P = 0.01, **P = 0.07; Anova analysis. Limit of detection, 0.2 pmol/mg protein.

WT tissues containing primarily lymphoid or myeloid cells, such as spleen, thymus and lymphoid deficient bone marrow (myeloid cells), had easily detectable levels of cADPR. In contrast, cADPR was not detected in lymphoid or myeloid tissues isolated from CD38KO mice. However, the cADPR content of CD38KO tissues such as brain, kidney and heart was nearly equivalent to the cADPR content of the same WT tissues. Thus, other unknown cyclases must be responsible for cADPR production in organs such as brain and heart, however, CD38 is the predominant ADP-ribosyl-cyclase expressed by myeloid and lymphoid cells.

CD38 deficient mice are more susceptible to bacterial infection. To test the requirement for CD38 and cADPR in innate inflammatory immune responses, CD38KO and WT mice were infected with *Streptococcus pneumoniae* and assessed survival (FIG. 7A). It was observed that the LD50 for CD38 KO animals is at least 10-fold lower than for WT mice, as 100 colony forming units (CFU) killed 50% of the CD38KO mice within 2.5 days of infection, while 1000 CFU were required to kill 50% of the WT animals in the same time period.

Since CD38 is expressed by the responding immunocytes and the bronchial epithelium (Fernandez J E et al., J. biol Reg Homeost Agents 12:81–91), WT or CD38KO bone marrow was transplanted into irradiated WT hosts to test whether CD38 expression in the lung and/or immune system was necessary for protection. The reconstituted chimeric animals possessed either CD38+ or CD38-deficient bone-marrow derived cells, while all other cell types, including the bronchial epithelium, were of WT origin in both groups of animals. The reconstituted mice were then infected with *S. pneumoniae* and survival was monitored (FIG. 7B). Reconstituted animals receiving CD38KO bone marrow were much more susceptible to infection compared to mice receiving WT bone marrow, indicating that the increased susceptibility of CD38KO mice to *S. pneumoniae* infection is due to the loss of CD38 on bone marrow-derived lymphoid and/or myeloid cells.

To determine whether the increased susceptibility of CD38KO animals to *S. pneumoniae* was due to an inability to restrain bacterial growth and spreading to systemic sites, CD38KO and WT mice were infected with 1000 CFU of *S. pneumoniae* and bacterial titers were assessed in lung and blood 12 hours post-infection (FIG. 7C). The bacterial titer in the lungs of CD38KO mice was increased five-fold compared to WT controls. However, the bacterial burden in the blood of the CD38KO mice was 200–500 times greater than in WT mice, indicating that the bacteria rapidly disseminate in CD38KO mice.

To determine whether myeloid or lymphoid cells were responsible for the increased bacterial spreading, Rag-2 KO mice (Shin Kai, et al., 1992 Cell 68:855–867) (which lack lymphocytes but can express CD38 on all myeloid cells) and CD38-Rag-2 double knockout mice (which lack lymphocytes and cannot express CD38 on their myeloid cells) were infected with 1000 CFU *S. pneumoniae* and then bacterial titers were determined in lung and blood 12 hours later (FIG. 7C). The bacterial titers in the lungs and blood of the lymphoid-deficient CD38-Rag-2 double KO mice were as high as those seen in the CD38KO mice and were significantly increased when compared to Rag-2 KO or WT mice. Thus, CD38 deficient myeloid cells are responsible for the increased susceptibility of CD38KO mice to *S. pneumoniae*.

CD38 deficient neutrophils do not accumulate at sites of infection and inflammation. To test whether myeloid cells were appropriately recruited to the lungs of *S. pneumoniae*-infected CD38KO animals, CD38KO and WT mice were infected and then the cells that were recruited to the lung airways after infection were enumerated. The total number of cells in the airways of CD38KO and WT animals increased equivalently from 6 to 18 hours post-infection (FIG. 8A). However, neutrophils were the predominant cell type found in the lungs of WT animals 12–18 hours post-infection, while the cellular infiltrate in the lungs of the CD38KO animals was composed primarily of macrophages (FIGS. 8B–C). Thus, CD38 appears to be required for sustained recruitment of neutrophils to the site of infection and inflammation.

CD38 deficient neutrophils make a defective chemotactic response to the chemoattractant fMLP. Neutrophils migrate to sites of infection in response to gradients of chemokines and chemoattractants that are produced by the local cells and by the invading pathogen (Hub et al. 1996 Chemoattractant Ligands and Their Receptors (ed. Horuk) 301–325 (CRC Press, Boca Raton, Fla.); Servant G. et al., 2000 Science 287:1037–1040; Gao, J. L., 1999 J. Exp. Med 189:657–662). Chemoattractants rapidly activate neutrophils and induce random migration (chemokinesis). If a chemotactic gradient exists, the activated neutrophils polarize their leading edge toward the highest concentration of the gradient and migrate directionally16 (chemotaxis). It has been previously demonstrated that neutrophils home to sites of infection upon stimulation of their N-formylpeptide receptor (FPR) by bacterially-derived formylated peptides such as formyl-methionyl-leucyl-phenylalanine (fMLP). To test whether CD38KO neutrophils were defective in their ability to chemotax to fMLP, the ability of CD38KO and WT neutrophils to migrate by chemokinesis and chemotaxis in a transwell checkerboard assay was determined (Falk et al., 1980 J. Immunol. Methods 33:239–247) (FIG. 8D). When fMLP was absent from the top and bottom chamber, or when fMLP was placed only in the top chamber, few (<2300 cells), but equivalent numbers, of the CD38KO and WT neutrophils migrated to the bottom chamber. When an equal concentration of fMLP was present in the top and bottom chamber (chemokinesis conditions), increased, but similar, numbers of WT and CD38KO neutrophils migrated to the bottom chamber, indicating that activation-induced chemokinesis to fMLP was equivalent between CD38KO and WT neutrophils. When fMLP was present in the bottom chamber only (chemotaxis conditions), the migration of WT neutrophils to the bottom chamber was further increased. However, CD38KO neutrophils migrated only marginally better in the presence of a chemotactic gradient than in the absence of a fMLP gradient, indicating that CD38KO neutrophils can be activated to migrate by bacterial chemoattractants but are unable to follow the chemotactic gradient. To determine if this was a general property of CD38KO neutrophils, the same experiments were performed using the chemokine IL-8, which is a potent activator of neutrophils (Baggiolini et al., 1989 *J. Clin. Invest* 84:1045–1049). In contrast to what was observed with fMLP, the IL-8-induced chemotaxis of CD38KO and WT neutrophils was equivalent (FIG. 8D). Thus, these data indicate that CD38KO neutrophils make defective chemotactic responses to some, but not all, chemoattractants.

CD38 is expressed and enzymatically active on neutrophils. Since CD38KO neutrophils appear to have an intrinsic defect in chemotaxis, CD38 expression and enzyme activity on mouse and human neutrophils was determined. Neutrophils isolated from the bone marrow and blood of WT mice clearly expressed CD38 (FIG. 9A), and likewise, human peripheral blood neutrophils also expressed CD38 (FIG. 9B). Interestingly, when WT mice were injected intraperitoneally with the inflammatory agent, thioglycollate, CD38 expression increased significantly on the neutrophils isolated from the blood and peritoneal cavity (FIG. 9D). Next, to test whether CD38-expressing neutrophils can catalyze the cyclase reaction, WT and CD38KO neutrophils were incubated with the NAD+ analogue, nicotinamide guanine dinucleotide (NGD), and then measured the cyclization of NGD into the fluorescent compound cyclic GDP-ribose (Graeff et al., 1994 *J. Biol. Chem* 269:30260–30267) (cGDPR). As shown in FIG. 9C, WT neutrophils, but not CD38KO neutrophils, produced cGDPR rapidly upon incubation with NGD, indicating that CD38-expressing neutrophils are competent to produce cyclic nucleotides.

cADPR and ryanodine induce intracellular calcium release in neutrophils. Since cADPR induces intracellular calcium release through ryanodine receptor (RyR) gated stores (Galione et al. 1991 *Science* 253:1143–1146), it was tested whether the RyR/cADPR calcium signaling pathway was functional in neutrophils. RT-PCR analysis showed that neutrophils express mRNA for RyR3 (Sorrentino, V. et al., 1993 *TIPS* 14:98–103; Hakamata Y. et al., 1992 *FEBS Lett* 312:229–235), although at levels much lower than seen in the brain (FIG. 9D). To test whether the RyRs expressed by neutrophils were functional, intracellular calcium levels ($[Ca^{2+}]i$) were measured in neutrophils that were permeabilized in calcium-free buffer and then stimulated with ryanodine (FIG. 9E). A small, but reproducible, increase in $[Ca^{2+}]$ in ryanodine-stimulated neutrophils that could be blocked by the RyR inhibitor, ruthenium red was observed (Galione et al. 1991 *Science* 253:1143–1146). Next, to test whether cADPR could induce intracellular calcium release in neutrophils, neutrophils were permalized in calcium-free buffer and then stimulated the cells with purified cADPR (FIG. 9F). A small, but easily detectable, rise in intracellular free calcium was observed. No calcium release was observed when the cADPR was first hydrolyzed by heat inactivation (Lee et al., 1989 *J. Biol. Chem.* 264:1608–1615) or when the cells were pre-treated with 8-Br-cADPR, an inactive analogue of cADPR that competitively antagonizes cADPR binding to RyRs (Guse et al., 1994 *Annu. Rev. Immunol* 12:593–633). The specificity of the antagonist, 8-Br-cADPR, for cADPR mediated calcium release was further demonstrated by showing that 8-Br-cADPR was unable to block the accumulation of intracellular free calcium mediated by thapsigargin (FIG. 9G). Together, the data demonstrate that intracellular calcium can be released through RyR and cADPR-mediated mechanism in neutrophils.

CD38 catalyzed cADPR is required for extracellular calcium influx in fMLP-activated neutrophils. Signaling through chemokine/chemoattractant G-protein coupled receptors such as FPR and the IL-8 receptors results in increased $[Ca^{2+}]i$ due to a combination of intracellular calcium release and extracellular calcium influx (Murphy, P. M., 1994 *Annu. Rev. Immunol* 12:593–633; Demaurex N. et al., 1994 *Biochem J.* 297:595–601; Schorr W. et al., 1999 *Eur. J. Immunol* 29:897–904: Lew et al., 1989 *Eur. J. Clin. Invest.* 19:338–346). Since CD38KO neutrophils were defective in chemotaxis assays to fMLP and lacked the ability to produce the calcium mobilizing metabolite, cADPR, it was hypothesized that calcium mobilization in response to fMLP would be deficient in CD38KO neutrophils. To test this, CD38KO or WT neutrophils were stimulated with fM/P or IL-8 in calcium-free media and intracellular calcium release was measured (FIG. 10A). An immediate sharp rise in intracellular calcium was observed that gradually declined over next 5 minutes in fMLP-stimulated WT neutrophils. In contrast, in fMLP-stimulated CD38KO cells, the magnitude of $[Ca^{2+}]i$ after fMLP stimulation was reduced by approximately 20% and the $[Ca^{2+}]i$ declined to baseline at least 2 minutes earlier. Unlike the reduced $[Ca^{2+}]i$ found in fMLP-stimulated CD38KO neutrophils, the $[Ca^{2+}]i$ of IL-8 stimulated CD38KO and WT neutrophils was identical. Thus, these data suggested that CD38 may be necessary for optimal intracellular calcium release after fMLP, but not IL-8, stimulation.

Next, to assess whether CD38KO or WT neutrophils were stimulated with fMLP or IL-8 in calcium-containing media (FIG. 10B). When we added fMLP to WT neutrophils, a rapid increase in $[Ca^{2+}]i$, due to intracellular calcium release was observed, as well as a second extended, increase in $[Ca^{2+}]i$, due to extracellular calcium influx. In striking contrast, the calcium influx phase of the response was essentially ablated in the fMLP-stimulated CD38KO neutrophils. Interestingly, when WT and CD38KO neutrophils were stimulated with IL-8 in calcium containing media, it was found that IL-8 induced a equivalent immediate increase in $[Ca^{2+}]i$ that rapidly declined to baseline levels in both WT and CD38KO neutrophils, indicating that IL-8 did not induce extracellular calcium influx in either WT or CD38KO neutrophils.

To determine whether cADPR regulates calcium mobilization in fMLP stimulated neutrophils, CD38KO and WT neutrophils were preincubated with increasing concentrations of the cADPR antagonist, 8-Br-cADPR, and then stimulated with fMLP or IL-8 (FIG. 10C). When 8-Br-cADPR-treated WT cells were stimulated with fMLP, the release of intracellular calcium as well as the influx of extracellular calcium was reduced in a dose-dependent fashion to the levels seen in CD38KO cells. In contrast, addition of 8-Br-cADPR to IL-8 stimulated neutrophils had absolutely no effect on the $[Ca^{2+}]i$ of either WT or CD38KO neutrophils. Together, these data indicate that CD38-produced cADPR regulates intracellular calcium release and extracellular calcium influx in response to fMLP, and that neither CD38 nor cADPR are necessary for calcium mobilization in IL-8 stimulated neutrophils.

CD38 catalyzed cADPR is required for neutrophil chemotaxis to fMLP but not IL-8. To test whether cADPR-mediated calcium mobilization is required for chemotaxis to fMLP, WT neutrophils were preincubated with either EGTA or 8-Br-cADPR and then chemotaxis to fMLP or IL-8 in a checkerboard chemotaxis assay was measured (FIG. 10D). When WT neutrophils (no pre-treatment) were incubated with media in the top chamber and fMLP or IL-8 in the bottom chamber, the cells efficiently migrated to the bottom chamber. However, if the extracellular calcium was chelated with EGTA or if the cells were pre-treated with the cADPR antagonist, 8-Br-cADPR, chemotaxis of the WT neutrophils to fMLP was reduced by more than 80%. Importantly, EGTA or 8-Br-cADPR treatment had absolutely no effect on the ability of neutrophils to chemotax to IL-8. Thus, extracellular calcium influx, regulated by cADPR-mediated intracellular calcium release, is necessary for fMLP-induced chemotaxis of neutrophils.

An analogue of NAD+ inhibits neutrophil chemotaxis to fMLP, but not IL-8, in a CD38-dependent fashion. Since CD38 catalyzed cADPR appeared necessary for neutrophil chemotaxis to fMLP, it was predicted that chemotaxis could be inhibited by treating neutrophils with NAD+ analogues that could be converted by CD38 into antagonists of the cADPR signaling pathway. To test this prediction, neutrophils with pretreated with nicotinamide 8-bromoadenine dinucleotide (N(8-Br-A)D$^+$), a substrate that can be converted by CD38 into 8-Br-cADPR, the cADPR antagonist that was used in our earlier experiments. To first test whether N(8-Br-A)D$^+$ altered extracellular calcium influx in fMLP-activated neutrophils, WT neutrophils were pretreated with N(8-Br-A)D$^+$, the cells were stimulated with fMLP and then [Ca$^{2+}$]i was measured (FIG. 11A). N(8-Br-A)D$^+$ pre-treatment inhibited the entry of extracellular calcium in fMLP-treated neutrophils. Next, WT and CD38KO neutrophils were pretreated with N(8-Br-A)D$^+$ or left in media alone, followed by testing for their ability to chemotax to fMLP (FIG. 11B) or IL-8 (FIG. 11C). Untreated WT neutrophils chemotaxed to both fMLP and IL-8, while untreated CD38KO neutrophils could not chemotax to fMLP, but could chemotax to IL-8. Interestingly, pre-treatment of WT neutrophils with N(8-Br-A)D$^+$ severely reduced neutrophil chemotaxis to fMLP but had no effect on their ability to chemotax to IL-8. Pre-treatment of the CD38KO neutrophils with N(8-Br-A)D$^+$ had no effect on the chemotaxis of the CD38KO neutrophils to either fMLP or IL-8, indicating that the N(8-Br-A)D$^+$ induced inhibition of fMLP-mediated chemotaxis was CD38 dependent. Together, the data demonstrate that NAD$^+$ analogues can regulate calcium responses and chemotaxis of neutrophils in a CD38-dependent fashion.

7. EXAMPLE

Mouse Model of Allergic Lung Disease and Role of CD38

The subsection below describes data demonstrating that CD38-deficient eosinophils are unable to be recruited to the site of airway inflammation induced by allergens.

7.1. Materials and Methods

OVA priming and sensitization. C57BL/6 WT mice were immunized intraperitoneally with 20 µg chicken ovalbutnin (OVA) adsorbed to alum. Immunized mice were sacrificed 30 days post-immunization and the OVA-primed CD4 T cells were purified from the spleen using MACS magnetic beads that were directly conjugated with anti-CD4. Naive CD4 T cells were purified using anti-CD4 conjugated MACS beads from unimmunized C57BL/6 WT mice. Naive or OVA-primed T cells were injected intravenously into either C57BL/6 WT or CD38KO recipients at 1×10$^7$ CD4 T cells per mouse to generate 4 groups of 10 mice each indicated in FIGS. 11A and B. Recipient mice were then sensitized intratracheally with 10 µg OVA in PBS on each of 7 consecutive days immediately following T cell transfer. Mice were sacrificed on the eighth day after T cell transfer, and infiltrating cells were removed from the airways and alveoli of the lungs by broncheoalveolar lavage as described in Section 6.2.2, supra. Total cells were then enumerated by counting on a hemocytometer and differential cell counts were performed by centrifuging cells on to a glass slide, staining with Diff-Quick and identifying at least 200 cells per slide at 400×.

7.2. Results

To determine if CD38 controls the recruitment of cells other than neutrophils to the lung, a mouse model of allergic lung disease that mimics many of the properties of human asthma was used (Lloyd C M et al., 2001, Adv. Immunol. 77:263–295). An important component of asthma is airway inflammation, which is thought to be induced or exacerbated by the activities of eosinophils that have been recruited to the lung. Although eosinophils are primarily responsible for the pathology of asthma (Broide, D H et al., 1991, J. Allergy Clin. Immunol. 88:637–648), their recruitment and function appears to be controlled by T cells that have been primed to allergenic antigens (Gavett et al., 1994, Respir. Cell Mol. Biol. 10:587–593). Such T cells often produce type 2 cytokines, such as IL-4, IL5 and IL-13, as well as chemokines like eotaxin (Cohn, L. et al., 1988, J. Immunol. 161:3813–3816; Drazen JM et al., 1996, J. Exper Med. 183:1–5). To examine the ability of CD38 to regulate eosinophil recruitment independently of any effects of CD38 on T cell activation, WT mice were immunized with the antigen OVA. After 30 days, CD4 T cells from these OVA-primed mice were transferred to either WT or CD38KO recipients. As a control, naive CD4 T cells were transferred from unimmunized WT mice to either WT or CD38KO recipients. Recipient mice were then sensitized intratracheally with 10 µg of OVA in PBS on each of eight consecutive days immediately following T cell transfer. Mice were sacrificed on the ninth day after T cell transfer and the cells in the airways of the lungs were enumerated.

As seen in FIG. 12A, substantial numbers of neutrophils were recruited to the airways of WT mice regardless of whether they received naive or primed CD4 T cells. In contrast, although CD38KO trice that received primed T cells did have significantly more neutrophils in the airways than CD38KO mice that received naive T cells, relatively few neutrophils were recruited to the airways of CD38KO mice compared to the airways of WT mice. Thus, neutrophil recruitment to the lung in a model of allergic airway disease is also dependent on the expression of CD38.

Strikingly, the recruitment of eosinophils to the airways of OVA-sensitized mice was dependent on the presence of both primed CD4 T cells and the expression of CD38. As seen in FIG. 12B there was a 30-fold reduction in the numbers of eosinophils recruited to the lungs of CD38KO mice that had received primed CD4 T cells relative to that in WT mice that had received primed CD4 T cells and a 10-fold reduction in the numbers of eosinophils recruited to the airways of CD38KO mice that received naive CD4 T cells relative to that in WT mice that had received naive CD4 T cells. Therefore, the recruitment of eosinophils to the lung in a model of allergic airway disease is also dependent on CD38.

8. EXAMPLE

Cloning of *Schistosoma mansoni* CD38 Homologue

The subsection below describes the cloning and sequencing of a *S. mansoni* CD38 homologue referred to as SM38.

Helminths, such as *S. mansoni*, are broadly defined as worm parasites that infect and can cause pathogenesis in most invertebrates, vertebrates and plant species. The genus *Schistosoma* consists of parasitic flatworms whose definitive habitat is the bloodstream of warm-blooded vertebrates. Four species of *Schistosoma*, including *S. mansoni* cause disease in 200–400 million humans per year and kill up to 1 million people each year (WHO, 1996). Additionally, at least two *Schistosoma* species infect domesticated cattle and sheep causing serious economic losses. Thus, it would be beneficial to develop effective antibiotic drugs that could be used to treat infected humans and/or animals. The pathogenesis of *Schistosoma* infection is caused mainly by the deposition of eggs by the mature worm into various tissues and organs of humans and animals where granulomas then form leading to fibrosis and tissue damage. However, the cercariae (immature worm) and fully mature worm also release a number of proteins and lipid mediators that can also induce an immune inflammatory response (Fusco, A C et al., 1991, J. Paristol. 77:649–657). The treatment of choice in schistosomaisis is the drug praziquantel which appears to induce calcium influx across the tegument of the worm causing immediate muscle contraction and paralysis (Kohn, A B et al., 2001, J. Biol. Chem 276:36873–36876). Thus, drugs that modulate schistosome calcium responses, particularly within the muscle, might be effective in the treatment of this disease.

8.1. Material and Methods

8.1.1. Cloning of *Shistosoma Mansoni* CD38 Homologue

Primers were made corresponding to the EST sequence found in Genbank accession #AW017229. (5' primer: acatctttgtggtactgaatggctcgg (SEQ ID NO:12) and 3' primer: tgagtaatgtctcgacgtttgacctcg (SEQ ID NO:13)). *S. mansoni* cDNA libraries were obtained from Dr. Phillip LoVerde (SUNY, Buffalo), and were subjected to PCR using the primers indicated above. The library (1–20 $\mu$l) and dH2O were heated to 70° C. for 10 minutes and were then combined with the remainder of the PCR reagents and cycled. The cycles were: 95° C. 5 minutes, 1 cycle, followed by 95° C. 1 minute, 65° C. 1 minute and 72° C. 2 minutes for 35 cycles followed by 1 cycle at 72° C. for 5 minutes. The expected 330 bp band corresponding to EST AW017229 was isolated, TOPO cloned, and then used as a probe to screen 250,000 plaques from the *S. mansoni* cDNA library. Five positives were isolated and then subjected to 3 more rounds of screening in order to produce plaque pure clones. All five clones were fully sequenced on both strands. The nucleotide sequence and amino acid translation of four of the clones were identical (referred to as SM38). The stop codon and polyadenylation sites were identified in all of the SM38 clones, but the initiation methionine was not present in any of the clones. To obtain the 5' end of the SM38 gene, a single primer extension approach (NAR, 1994, vol 22, No. 16, p3427–3428) was utilized. A first round of PCR was performed using an external SM38 primer (5' catcgaataaccctgatttcataacac) (SEQ ID NO:14) and the universal reverse primer for Bluescript. Two $\mu$l of this reaction was then subjected to PCR using an internal nested SM38 primer (5' gataaagtaagaactcgtgcc) (SEQ ID NO:15) and the universal reverse primer. A 200 and a 300 bp band were identified from this reaction and were directly sequenced. The sequence obtained overlapped 124 bp with the 5' end of the SM38 clones are included an additional 153 bp of sequence, however the no stop codon was detected, indicating that we still did not have the 5' end of the gene. Therefore, classic 5"RACE (PNAS vol 85 pp 8998–9002, Dec. 1998) was performed using cDNA prepared from RNA isolated from adult *S. mansoni* worms (RNA provided by Dr. P. LoVerde, SUNY Buffalo). 10X Taq buffer, dNTP's, cDNA and Expand High Fidelity Taq were combined with the dT-AP primer (see ref. for details) and cycled for 5 minutes at 95° C. followed by 2 minutes at 50° C. and 40 minutes at 72° C. After this 40 minute incubation the 5' external SM38 primer (see above) and AP primers were added and cycled for 35 cycles under the conditions: 95° C. for 15 sec, 47° C. for 30 sec, 72° C. for 2 minutes followed by a 5 minute extension at 72° C. The reactions were run on a 1.5% agarose gel and a 300 bp band was isolated using Qiagen Gel Kit. The 5' RACE product was directly sequenced with the AP and 5' external SM38 primer. Two potential initiation methionines were identified in the sequence and two stop codons were found 13–19 amino acids upstream of the methionine residues. The RACE product was subsequently cloned. All three clones containing SM38 sequence (two PCR generated clones and one clone from the *S.mansoni* cDNA library) were contiguous and overlapping. When assembled, the SM38 sequence included 1049 bp of sequence including 5' untranslated sequence, two potential initiation methionines, an open reading frame encoding a 303 amino acid protein, a stop codon, 3' untranslated sequence and a poly-adenylation site.

8.2. Results

Since drugs that modulate calcium responses in the muscle fibers of Schistosomes appear to be effective anti-helminth reagents (Kohn et al, 2001, J. Biol. Chem. 276:36873–36876), we set out to identify specific calcium modulating targets of Schistosomes. It has been recently shown that Schistosomes express Ryanodine Receptors (RyR) within their muscle fibers (Day et al., 2000, Parasitol. 120:417–420; Silva et al., 1998, Biochem. Pharmacol. 56:997–1003). Agonists of RyRs expressed in vertebrate smooth and skeletal muscle are known to regulate intracellular calcium release, voltage gated calcium influx and muscle contractility. Interestingly, *S. mansoni* muscle fibers treated with RyR agonists such as caffeine induced the release of intracellular calcium and induced contraction of the muscle fiber. Although drugs such as caffeine can modulate RyR-dependent calcium responses, the physiological modulator of RyRs, at least in vertebrate muscle fibers is cyclic ADP-ribose (cADPR). cADPR is a known calcium mobilizing metabolite that is produced by ADP-ribosyl cyclase enzymes such as the mammalian CD38 protein and the invertebrate Aplysia cyclase enzyme. To determine whether Schistosomes express an enzyme capable of producing the calcium mobilizing second messenger, cADPR, a search was performed of the publicly available EST sequences looking for Schistosome sequences that when translated would have homology to the mammalian CD38 and Aplysia enzymes. Three EST sequences (EST AI067047, EST AW017229 and EST N20756) were identified that could be assembled into a contiguous and overlapping sequence (FIG. 13). This assembled sequence shared limited but significant homology with both CD38 and the Aplysia cyclase enzymes.

To determine whether the assembled ESTs actually represented an authentic cDNA, primers were prepared from the sequence of EST AW017229 and performed PCR on a *S. mansoni* cDNA library. A 330 base pair fragment was isolated from the PCR reaction and was sequenced. As expected the sequence of the fragment matched that of the EST. The fragment was then used as a probe to screen 250,000 plaques from the *S. mansoni* cDNA library. Five independent plaques which hybridized to the EST probe were isolated, plaque purified and sequenced on both DNA strands. The sequence information was then used to design additional primers to isolate the 5' end of the cDNA (see methods). The complete cDNA sequence isolated from the *S. mansoni* library was then assemble and compared to the ESTs. The alignment, shown in FIG. 13, indicates that the contiguous assembly of the EST sequences was correct and that the cloned cDNA (referred to as SM38) included at least an additional 421 base pairs of sequence not found in any EST. Translation of the DNA sequence gave rise to a 299 amino acid sequence (FIG. 14) containing structural motifs typical of cyclase enzymes (Prasad, G S, 1996 Nature Struct. biol. 3:957–964). In particular, the SM38 protein contains conserved amino acid residues that align with critical catalytic and active site residues found in the Aplysia cyclase enzyme (Munshi C, et al., 1999, J. Biol. Chem. 274:30770–30777) and in mammalian CD38 (Munshi C, et al., 2000, J. Biol. Chem. 275:21566–21571; Graeff R., 2001, J. Biol. Chem. 276:12169–12173)(FIGS. 15A–B). Additionally, cysteine residues that are critical for the assembly of the tertiary structure of the cyclase enzymes (Prasad G S, et al., 1996, NAture Struct. biol. 3:957–964)are also conserved in SM38; (FIGS. 15A–B). Importantly, the SM38 cDNA sequence encodes for a complete cyclase enzyme domain (FIG. 16).

Based on these results, we have shown that Schistosomes such as *S. mansoni* encode a protein (SM38) that is highly homologous at the structural level to enzymes that are capable of catalyzing the production of the calcium mobilizing second messenger, cADPR. Since Schistosomes also express RyRs which release intracellular calcium in response to cADPR, it is predicted that SM38 will be able to regulate calcium response in Schistosomes. Furthermore, since regulation of calcium influx, particularly in Schistosome muscle fibers can result in paralysis and clearance of the worm, we predict that agonists/antagonists of the SM38 and RyR pathways in *Schistosomes* may be effective as anti-helminth drugs.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

We claim:

1. A method for identifying a compound that inhibits CD38 enzyme activity comprising (i) contacting a cell expressing CD38 and a chemoattractant receptor with a test compound in the presence of a chemoattractant and substrate and measuring the level of CD38 activity; (ii) in a separate experiment, contacting a cell expressing CD38 and a chemoattractant receptor with a vehicle control in the presence of a chemoattractant and substrate and measuring the level of CD38 activity where the conditions are essentially the same as in part (i); and then (iii) comparing the level of CD38 activity measured in part (i) with the level of CD38 activity in part (ii), wherein a decrease in the level of CD38 activity in the presence of the test compound indicates that the test compound is a CD38 inhibitor.

2. The method of claim 1 wherein CD38 mediated cell migration is measured.

3. The method of claim 1, wherein the CD38 enzyme activity is selected from the group consisting of $NAD^+$ glycohydrolase activity, ADP-ribosyl cyclase activity, and transglycosidation activity.

4. The method of claim 3, wherein enzyme activity is measured by monitoring the rate of formation of nicotinamide, ADP-ribose (ADPR), cyclic-ADPR (cADPR), or nicotinic acid adenine dinucleotide phosphate (NAADP).

5. The method of claim 1, wherein the chemoattractant is selected from the group consisting of fMet-Leu-Phe (fMLP), eotaxin, growth-regulated oncogene-1 (GRO-1), interferon-gamma inducible protein-10 kDa (IP-10), stromal cell-derived factor-1 (SDF-1), B lymphocyte chemoattractant (BLC), chemokine ligand-5 (CCL5; Rantes), macrophage-inflammatory protein-1A (MIP-1A), monocyte chemoattractant protein-3 (MCP-3), macrophage-inflammatory protein-3a (MIP3a), interleukin-8 (IL-8), CLS, macrophage-inflammatory protein-3beta (MIP3β; ELC), lymphotactin, platelet-activating factor (PAF), leukotriene B4 (Ltb4), complement c5a, and histamine.

* * * * *

UNITED STATES PATENT AND TRADEMARK OFFICE
CERTIFICATE OF CORRECTION

| | | Page 1 of 1 |
|---|---|---|
| PATENT NO. | : 6,955,884 B2 | |
| APPLICATION NO. | : 09/982616 | |
| DATED | : October 18, 2005 | |
| INVENTOR(S) | : Frances E. Lund et al. | |

It is certified that error appears in the above-identified patent and that said Letters Patent is hereby corrected as shown below:

Column 1, line 4 after the title, please insert:

--FEDERAL FUNDING

This invention was made with government support under grant/contract number AI043629 awarded by the National Institute of Health. The government has certain rights to the invention.--

Signed and Sealed this
Twenty-first Day of June, 2011

David J. Kappos
*Director of the United States Patent and Trademark Office*

SEQUENCE LISTING

<160> NUMBER OF SEQ ID NOS: 15

<210> SEQ ID NO 1
<211> LENGTH: 1073
<212> TYPE: DNA
<213> ORGANISM: Shistosoma mansoni

<400> SEQUENCE: 1

```
ggaaagaacg tagacatata ttgttatata gatttgttca gttattttc acaatctttt      60 aattcaaata atgatgaacg taatattgtt tcttacttta tcaaatattt ttgtctttaa     120
ctctgcacaa catcaaataa acttacttag tgaaatagta caatcacgat gtactcagtg     180
gaaggttgaa catggagcta ctaatataag ttgtagtgag atctggaatt catttgaaag     240
cattttactt tcaactcata ctaaatcagc atgtgttatg aaatcagggt tattcgatga     300
ttttgtttat caattgtttg aattggaaca acaacaacaa cagcgacacc acacaattca     360
aacggaacaa tacttccatt ctcaagtgat gaacatcatt cgtggaatgt gtaaacgtct     420
tggagtatgt cgttctctag aaactacatt tccaggatat ctgtttgatg aattgaattg     480
gtgtaatggc agtttaacag gcaacacaaa atacgggact gtatgtggat gcgattataa     540
aagtaatgtt gttcatgcgt tctggcaaag tgcttcggct gagtatgcca ggagagcatc     600
tggtaacatc tttgtggtac tgaatggctc ggtcaaagct ccatttaatg aaaataaaac     660
ttttggaaaa atagaactac cattgttaaa acatcctcga gtacaacaat taacagtgaa     720
attagttcat agtttggaag atgtaaataa ccgacaaaca tgtgaatcgt ggagtctgca     780
agaacttgca aacaagctga actctgtaca tattcctttt cgttgcattg acgatccttt     840
agagttcaga cattatcaat gcattgaaaa tcctggcaaa caactatgtc agttttcagc     900
ttcgacgagg tcaaacgtcg agacattact catactttt ccgctagtca tttgtttaac      960
```

-continued

```
tttttatact tccatgaatt gaaataactt ttcagaacta aactttgaac agagaaagag      1020
aacaatgata ataaggaat aggacattaa tgaaaaaaaa aaaaaaaaaa aaa             1073
```

<210> SEQ ID NO 2
<211> LENGTH: 353
<212> TYPE: PRT
<213> ORGANISM: Shistosoma mansoni

<400> SEQUENCE: 2

```
Glu Arg Thr Thr Tyr Ile Val Ile Ile Cys Ser Val Ile Phe His Asn
 1               5                  10                  15

Leu Leu Ile Gln Ile Met Met Asn Val Ile Leu Phe Leu Thr Leu Ser
             20                  25                  30

Asn Ile Phe Val Phe Asn Ser Ala Gln His Gln Ile Asn Leu Leu Ser
         35                  40                  45

Glu Ile Val Gln Ser Arg Cys Thr Gln Trp Lys Val Glu His Gly Ala
     50                  55                  60

Thr Asn Ile Ser Cys Ser Glu Ile Trp Asn Ser Phe Glu Ser Ile Leu
 65                  70                  75                  80

Leu Ser Thr His Thr Lys Ser Ala Cys Val Met Lys Ser Gly Leu Phe
                 85                  90                  95

Asp Asp Phe Val Tyr Gln Leu Phe Glu Leu Glu Gln Gln Gln Gln Gln
            100                 105                 110

Arg His His Thr Ile Gln Thr Glu Gln Tyr Phe His Ser Gln Val Met
        115                 120                 125

Asn Ile Ile Arg Gly Met Cys Lys Arg Leu Gly Val Cys Arg Ser Leu
    130                 135                 140

Glu Thr Thr Phe Pro Gly Tyr Leu Phe Asp Glu Leu Asn Trp Cys Asn
145                 150                 155                 160

Gly Ser Leu Thr Gly Asn Thr Lys Tyr Gly Thr Val Cys Gly Cys Asp
                165                 170                 175

Tyr Lys Ser Asn Val Val His Ala Phe Trp Gln Ser Ala Ser Ala Glu
            180                 185                 190

Tyr Ala Arg Arg Ala Ser Gly Asn Ile Phe Val Val Leu Asn Gly Ser
        195                 200                 205

Val Lys Ala Pro Phe Asn Glu Asn Lys Thr Phe Gly Lys Ile Glu Leu
    210                 215                 220

Pro Leu Leu Lys His Pro Arg Val Gln Gln Leu Thr Val Lys Leu Val
225                 230                 235                 240

His Ser Leu Glu Asp Val Asn Asn Arg Gln Thr Cys Glu Ser Trp Ser
                245                 250                 255

Leu Gln Glu Leu Ala Asn Lys Leu Asn Ser Val His Ile Pro Phe Arg
            260                 265                 270

Cys Ile Asp Asp Pro Leu Glu Phe Arg His Tyr Gln Cys Ile Glu Asn
        275                 280                 285

Pro Gly Lys Gln Leu Cys Gln Phe Ser Ala Ser Thr Arg Ser Asn Val
    290                 295                 300

Glu Thr Leu Leu Ile Leu Phe Pro Leu Val Ile Cys Leu Thr Phe Tyr
305                 310                 315                 320

Thr Ser Met Asn Asn Phe Ser Glu Leu Asn Phe Glu Gln Arg Lys
                325                 330                 335

Arg Thr Met Ile Ile Lys Glu Asp Ile Asn Glu Lys Lys Lys Lys
            340                 345                 350
```

<210> SEQ ID NO 3
<211> LENGTH: 1050
<212> TYPE: DNA
<213> ORGANISM: Artificial Sequence
<220> FEATURE:
<223> OTHER INFORMATION: SM38 consensus sequence

<400> SEQUENCE: 3

```
ggaaagaacg tagacatata ttgttatata gatttgttca gttattttc acaatctttt        60
aattcaaata atgatgaacg taatattgtt tcttacttta tcaaatattt ttgtctttaa      120
ctctgcacaa catcaaataa acttacttag tgaaatagta caatcacgat gtactcagtg      180
gaaggttgaa catggagcta ctaatataag ttgtagtgag atctggaatt catttgaaag      240
cattttactt tcaactcata ctaaatcagc atgtgttatg aaatcagggt tattcgatga      300
ttttgtttat caattgtttg aattggaaca acaacaacaa cagcgacacc acacaattca      360
aacggaacaa tacttccatt ctcaagtgat gaacatcatt cgtggaatgt gtaaacgtct      420
tggagtatgt cgttctctag aaactacatt tccaggatat ctgtttgatg aattgaattg      480
gtgtaatggc agtttaacag gcaacacaaa atacgggact gtatgtggat gcgattataa      540
aagtaatgtt gttcatgcgt tctggcaaag tgcttcggct gagtatgcca ggagagcatc      600
tggtaacatc tttgtggtac tgaatggctc ggtcaaagct ccatttaatg aaaataaaac      660
ttttggaaaa atagaactac cattggttaa aacatcctcg agtacaacaa ttaacagtga      720
aattagttca tagtttggaa gatgtaaata accgacaaac atgtgaatcg tggagtctgc      780
aagaacttgc aaacaagctg aactctgtac atattccttt tcgttgcatt gacgatcctt      840
tagagttcag acattatcaa tgcattgaaa atcctggcaa acaactatgt cagttttcag      900
cttcgacgag gtcaaacgtc gagacattac tcatactttt tccgctagtc atttgtttaa      960
ctttttatac ttccatgaat tgaaataact tttcagaact aaactttgaa cagagaaaga     1020
gaacaatgat aataaaggaa taggmcatta                                      1050
```

<210> SEQ ID NO 4
<211> LENGTH: 473
<212> TYPE: DNA
<213> ORGANISM: Shistosoma mansoni

<400> SEQUENCE: 4

```
ggctgagtat gccaggagag catctggtaa catctttgtg gtactgaatg gctcggtcaa       60
agctccattt aatgaaaata aaacttttgg aaaatagaa ctaccattgt taaaacatcc      120
tcgagtacaa caattaacag tgaaattagt tcatagtttg gaagatgtaa ataaccgaca      180
aacatgtgaa tcgtggagtc tgcaagaact tgcaaacaag ctgaactctg tacatattcc      240
ttttcgttgc attgacgatc ctttagagtt cagacattat caatgcattg aaaatcctgg      300
caaacaacta tgtcagtttt cagcttcgac gaggtcaaac gtcgagacat tactcatact      360
ttttccgcta gtcatttgtt taactttta tacttccatg aattgaaata acttttcaga      420
actaaacttt gaacagagaa agagaacaat gataataaag gaataggcca tta            473
```

<210> SEQ ID NO 5
<211> LENGTH: 145
<212> TYPE: DNA
<213> ORGANISM: Shistosoma mansoni

<400> SEQUENCE: 5

```
attgaaaatc atggcaaaca actatgtcag ttttcagctt cgacgaggtc aaacgtcgag    60
acattactca tacttttttcc gctagtcatt tgtttaactt tttatacttc catgaattga   120
aataactttt cagaactaaa ctttg                                          145

<210> SEQ ID NO 6
<211> LENGTH: 280
<212> TYPE: DNA
<213> ORGANISM: Shistosoma mansoni

<400> SEQUENCE: 6
ggagtatgtc gttctctaga aactacattt ccaggatatc tgtttgatga attgaattgg    60
tgcaatggca gtttaacagg caacacaaaa tacgggactg tatgtggatg cgattataaa   120
agtaatgttg ttcatgcgtt ctggcaaagt gcttcggctg agtatgccag agagcatct    180 ggtaacatct ttgtggtact gaatggctcg gtcaaagctc catttaatga aaataaaact   240
tttggaaaaa tagaactacc attggttaaa acatcctcga                         280

<210> SEQ ID NO 7
<211> LENGTH: 1049
<212> TYPE: DNA
<213> ORGANISM: Shistosoma mansoni

<400> SEQUENCE: 7
ggaaagaacg tagacatata ttgttatata gatttgttca gttattttc acaatctttt     60 aattcaaata atgatgaacg taatattgtt tcttacttta tcaaatattt ttgtctttaa   120
ctctgcacaa catcaaataa acttacttag tgaaatagta caatcacgat gtactcagtg   180
gaaggttgaa catggagcta ctaatataag ttgtagtgag atctggaatt catttgaaag   240
cattttactt tcaactcata ctaaatcagc atgtgttatg aaatcagggt tattcgatga   300
ttttgtttat caattgtttg aattggaaca acaacaacaa cagcgacacc acacaattca   360
aacggaacaa tacttccatt ctcaagtgat gaacatcatt cgtggaatgt gtaaacgtct   420
tggagtatgt cgttctctag aaactacatt tccaggatat ctgtttgatg aattgaattg   480
gtgtaatggc agtttaacag gcaacacaaa atacgggact gtatgtggat gcgattataa   540
aagtaatgtt gttcatgcgt tctggcaaag tgcttcggct gagtatgcca ggagagcatc   600
tggtaacatc tttgtggtac tgaatggctc ggtcaaagct ccatttaatg aaaataaaac   660
ttttggaaaa atagaactac cattgttaaa acatcctcga gtacaacaat aacagtgaa    720 attagttcat agtttggaag atgtaaataa ccgacaaaca tgtgaatcgt ggagtctgca   780
agaacttgca aacaagctga actctgtaca tattcctttt cgttgcattg acgatccttt   840
agagttcaga cattatcaat gcattgaaaa tcctggcaaa caactatgtc agttttcagc   900
ttcgacgagg tcaaacgtcg agacattact catacttttt ccgctagtca tttgtttaac   960
tttttatact tccatgaatt gaaataactt ttcagaacta aactttgaac agagaaagag  1020
aacaatgata ataaaggaat aggacatta                                    1049

<210> SEQ ID NO 8
<211> LENGTH: 282
<212> TYPE: PRT
<213> ORGANISM: Aplysia californica

<400> SEQUENCE: 8

Met Ser Pro Val Ala Ile Val Ala Cys Val Cys Leu Ala Val Thr Leu
 1               5                  10                  15
```

-continued

```
Thr Arg Ile Ser Pro Ser Glu Ala Ile Phe Pro Thr Pro Glu Leu Gln
             20                  25                  30

Asn Val Phe Leu Gly Arg Cys Lys Asp Tyr Glu Ile Thr Arg Tyr Leu
         35                  40                  45

Thr Ile Leu Pro Arg Val Lys Ser Asp Cys Arg Ala Leu Trp Thr Asn
     50                  55                  60

Phe Phe Lys Ala Phe Ser Phe Lys Ala Pro Cys Asn Leu Asp Leu Gly
 65                  70                  75                  80

Ser Tyr Lys Asp Phe Phe Gln Arg Ala Gln Gln Thr Leu Pro Lys Asn
                 85                  90                  95

Lys Val Met Phe Trp Ser Gly Val Tyr Asp Glu Ala His Asp Phe Ala
            100                 105                 110

Asp Asp Gly Arg Lys Tyr Ile Thr Leu Glu Asp Thr Leu Pro Gly Tyr
        115                 120                 125

Met Leu Asn Ser Leu Val Trp Cys Gly Gln Arg Asp Lys Pro Gly Phe
    130                 135                 140

Asn Gln Lys Val Cys Pro Asp Phe Lys Asp Cys Pro Val Gln Ala Arg
145                 150                 155                 160

Glu Ser Phe Trp Gly Thr Ala Ser Ser Tyr Ala His Ser Ala Glu
                165                 170                 175

Gly Asp Val Thr Tyr Met Val Asp Gly Ser Asn Pro Lys Val Pro Ala
            180                 185                 190

Tyr Arg Pro Asp Ser Phe Phe Gly Lys Tyr Glu Leu Pro Asn Leu Thr
        195                 200                 205

Asn Lys Val Thr Lys Val Lys Val Ile Val Leu His Gln Leu Gly Gln
    210                 215                 220

Lys Ile Ile Glu Arg Cys Gly Ala Gly Ser Leu Leu Asp Leu Glu Met
225                 230                 235                 240

Val Val Lys Ala Lys Lys Phe Gly Phe Asp Cys Val Glu Asn Pro Lys
                245                 250                 255

Ser Val Leu Phe Leu Leu Cys Ala Asp Asn Pro Asn Ala Arg Glu Cys
            260                 265                 270

Gln Leu Ala Lys Arg Tyr Tyr Arg Ile Ala
        275                 280
```

<210> SEQ ID NO 9
<211> LENGTH: 300
<212> TYPE: PRT
<213> ORGANISM: Homo sapien

<400> SEQUENCE: 9

```
Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val
             20                  25                  30

Leu Ile Leu Val Val Val Leu Ala Val Val Pro Arg Trp Arg Gln
         35                  40                  45

Gln Trp Ser Gly Pro Gly Thr Thr Lys Arg Phe Pro Glu Thr Val Leu
     50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
```

-continued

```
                100                 105                 110
Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
        180                 185                 190

Ser Arg Arg Phe Ala Glu Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
        260                 265                 270

Phe Ser Cys Lys Asn Ile Tyr Arg Pro Asp Lys Phe Leu Gln Cys Val
        275                 280                 285

Lys Asn Pro Glu Asp Ser Cys Thr Ser Glu Ile
290                 295                 300

<210> SEQ ID NO 10
<211> LENGTH: 303
<212> TYPE: PRT
<213> ORGANISM: Shistosoma mansoni

<400> SEQUENCE: 10

Met Met Asn Val Ile Leu Phe Leu Thr Leu Ser Asn Ile Phe Val Phe
1               5                   10                  15

Asn Ser Ala Gln His Gln Ile Asn Leu Leu Ser Glu Ile Val Gln Ser
                20                  25                  30

Arg Cys Thr Gln Trp Lys Val Glu His Gly Ala Thr Asn Ile Ser Cys
        35                  40                  45

Ser Glu Ile Trp Asn Ser Phe Glu Ser Ile Leu Leu Ser Thr His Thr
50                  55                  60

Lys Ser Ala Cys Val Met Lys Ser Gly Leu Phe Asp Asp Phe Val Tyr
65                  70                  75                  80

Gln Leu Phe Glu Leu Glu Gln Gln Gln Gln Arg His His Thr Ile
                85                  90                  95

Gln Thr Glu Gln Tyr Phe His Ser Gln Val Met Asn Ile Ile Arg Gly
                100                 105                 110

Met Cys Lys Arg Leu Gly Val Cys Arg Ser Leu Glu Thr Thr Phe Pro
        115                 120                 125

Gly Tyr Leu Phe Asp Glu Leu Asn Trp Cys Asn Gly Ser Leu Thr Gly
130                 135                 140

Asn Thr Lys Tyr Gly Thr Val Cys Gly Cys Asp Tyr Lys Ser Asn Val
145                 150                 155                 160

Val His Ala Phe Trp Gln Ser Ala Ser Ala Glu Tyr Ala Arg Arg Ala
                165                 170                 175
```

-continued

```
Ser Gly Asn Ile Phe Val Val Leu Asn Gly Ser Val Lys Ala Pro Phe
            180                 185                 190

Asn Glu Asn Lys Thr Phe Gly Lys Ile Glu Leu Pro Leu Leu Lys His
        195                 200                 205

Pro Arg Val Gln Gln Leu Thr Val Lys Leu Val His Ser Leu Glu Asp
    210                 215                 220

Val Asn Asn Arg Gln Thr Cys Glu Ser Trp Ser Leu Gln Glu Leu Ala
225                 230                 235                 240

Asn Lys Leu Asn Ser Val His Ile Pro Phe Arg Cys Ile Asp Asp Pro
                245                 250                 255

Leu Glu Phe Arg His Tyr Gln Cys Ile Glu Asn Pro Gly Lys Gln Leu
            260                 265                 270

Cys Gln Phe Ser Ala Ser Thr Arg Ser Asn Val Glu Thr Leu Leu Ile
        275                 280                 285

Leu Phe Pro Leu Val Ile Cys Leu Thr Phe Tyr Thr Ser Met Asn
    290                 295                 300

<210> SEQ ID NO 11
<211> LENGTH: 909
<212> TYPE: PRT
<213> ORGANISM: Artificial Sequence
<220> FEATURE:
<223> OTHER INFORMATION: Reverse translation of SM38

<400> SEQUENCE: 11

Ala Thr Gly Ala Thr Gly Ala Ala Tyr Gly Thr Asn Ala Thr His Tyr
 1               5                  10                  15

Thr Asn Thr Thr Tyr Tyr Thr Asn Ala Cys Asn Tyr Thr Asn Trp Ser
            20                  25                  30

Asn Ala Ala Tyr Ala Thr His Thr Thr Tyr Gly Thr Asn Thr Thr Tyr
        35                  40                  45

Ala Ala Tyr Trp Ser Asn Gly Cys Asn Cys Ala Arg Cys Ala Tyr Cys
    50                  55                  60

Ala Arg Ala Thr His Ala Ala Tyr Tyr Thr Asn Tyr Thr Asn Trp Ser
65                  70                  75                  80

Asn Gly Ala Arg Ala Thr His Gly Thr Asn Cys Ala Arg Trp Ser Asn
                85                  90                  95

Met Gly Asn Thr Gly Tyr Ala Cys Asn Cys Ala Arg Thr Gly Gly Ala
            100                 105                 110

Ala Arg Gly Thr Asn Gly Ala Arg Cys Ala Tyr Gly Gly Asn Gly Cys
        115                 120                 125

Asn Ala Cys Asn Ala Ala Tyr Ala Thr His Trp Ser Asn Thr Gly Tyr
    130                 135                 140

Trp Ser Asn Gly Ala Arg Ala Thr His Thr Gly Gly Ala Ala Tyr Trp
145                 150                 155                 160

Ser Asn Thr Thr Tyr Gly Ala Arg Trp Ser Asn Ala Thr His Tyr Thr
                165                 170                 175

Asn Tyr Thr Asn Trp Ser Asn Ala Cys Asn Cys Ala Tyr Ala Cys Asn
            180                 185                 190

Ala Ala Arg Trp Ser Asn Gly Cys Asn Thr Gly Tyr Gly Thr Asn Ala
        195                 200                 205

Thr Gly Ala Ala Arg Trp Ser Asn Gly Gly Asn Tyr Thr Asn Thr Thr
    210                 215                 220

Tyr Gly Ala Tyr Gly Ala Tyr Thr Thr Tyr Gly Thr Asn Thr Ala Tyr
225                 230                 235                 240
```

-continued

```
Cys Ala Arg Tyr Thr Asn Thr Thr Tyr Gly Ala Arg Tyr Thr Asn Gly
                245                 250                 255

Ala Arg Cys Ala Arg Cys Ala Arg Cys Ala Arg Cys Ala Arg Cys Ala
            260                 265                 270

Arg Met Gly Asn Cys Ala Tyr Cys Ala Tyr Ala Cys Asn Ala Thr His
        275                 280                 285

Cys Ala Arg Ala Cys Asn Gly Ala Arg Cys Ala Arg Thr Ala Tyr Thr
    290                 295                 300

Thr Tyr Cys Ala Tyr Trp Ser Asn Cys Ala Arg Gly Thr Asn Ala Thr
305                 310                 315                 320

Gly Ala Ala Tyr Ala Thr His Ala Thr His Met Gly Asn Gly Gly Asn
                325                 330                 335

Ala Thr Gly Thr Gly Tyr Ala Ala Arg Met Gly Asn Tyr Thr Asn Gly
            340                 345                 350

Gly Asn Gly Thr Asn Thr Gly Tyr Met Gly Asn Trp Ser Asn Tyr Thr
        355                 360                 365

Asn Gly Ala Arg Ala Cys Asn Ala Cys Asn Thr Thr Tyr Cys Cys Asn
    370                 375                 380

Gly Gly Asn Thr Ala Tyr Tyr Thr Asn Thr Thr Tyr Gly Ala Tyr Gly
385                 390                 395                 400

Ala Arg Tyr Thr Asn Ala Ala Tyr Thr Gly Gly Thr Gly Tyr Ala Ala
                405                 410                 415

Tyr Gly Gly Asn Trp Ser Asn Tyr Thr Asn Ala Cys Asn Gly Gly Asn
            420                 425                 430

Ala Ala Tyr Ala Cys Asn Ala Ala Arg Thr Ala Tyr Gly Gly Asn Ala
        435                 440                 445

Cys Asn Gly Thr Asn Thr Gly Tyr Gly Gly Asn Thr Gly Tyr Gly Ala
    450                 455                 460

Tyr Thr Ala Tyr Ala Ala Arg Trp Ser Asn Ala Ala Tyr Gly Thr Asn
465                 470                 475                 480

Gly Thr Asn Cys Ala Tyr Gly Cys Asn Thr Thr Tyr Thr Gly Gly Cys
                485                 490                 495

Ala Arg Trp Ser Asn Gly Cys Asn Trp Ser Asn Gly Cys Asn Gly Ala
            500                 505                 510

Arg Thr Ala Tyr Gly Cys Asn Met Gly Asn Met Gly Asn Gly Cys Asn
        515                 520                 525

Trp Ser Asn Gly Gly Asn Ala Ala Tyr Ala Thr His Thr Thr Tyr Gly
530                 535                 540

Thr Asn Gly Thr Asn Tyr Thr Asn Ala Ala Tyr Gly Gly Asn Trp Ser
545                 550                 555                 560

Asn Gly Thr Asn Ala Ala Arg Gly Cys Asn Cys Asn Thr Thr Tyr
                565                 570                 575

Ala Ala Tyr Gly Ala Arg Ala Ala Tyr Ala Ala Arg Ala Cys Asn Thr
            580                 585                 590

Thr Tyr Gly Gly Asn Ala Ala Arg Ala Thr His Gly Ala Arg Tyr Thr
        595                 600                 605

Asn Cys Cys Asn Tyr Thr Asn Tyr Thr Asn Ala Ala Arg Cys Ala Tyr
    610                 615                 620

Cys Cys Asn Met Gly Asn Gly Thr Asn Cys Ala Arg Cys Ala Arg Tyr
625                 630                 635                 640

Thr Asn Ala Cys Asn Gly Thr Asn Ala Ala Arg Tyr Thr Asn Gly Thr
                645                 650                 655

Asn Cys Ala Tyr Trp Ser Asn Tyr Thr Asn Gly Ala Arg Gly Ala Tyr
```

```
                      660                 665                 670
Gly Thr Asn Ala Ala Tyr Ala Tyr Met Gly Asn Cys Ala Arg Ala
            675                 680                 685
Cys Asn Thr Gly Tyr Gly Ala Arg Trp Ser Asn Thr Gly Trp Ser
            690                 695                 700
Asn Tyr Thr Asn Cys Ala Arg Gly Ala Arg Tyr Thr Asn Gly Cys Asn
705                 710                 715                 720
Ala Ala Tyr Ala Ala Arg Tyr Thr Asn Ala Ala Tyr Trp Ser Asn Gly
                725                 730                 735
Thr Asn Cys Ala Tyr Ala Thr His Cys Cys Asn Thr Thr Tyr Met Gly
            740                 745                 750
Asn Thr Gly Tyr Ala Thr His Gly Ala Tyr Gly Ala Tyr Cys Cys Asn
            755                 760                 765
Tyr Thr Asn Gly Ala Arg Thr Thr Tyr Met Gly Asn Cys Ala Tyr Thr
            770                 775                 780
Ala Tyr Cys Ala Arg Thr Gly Tyr Ala Thr His Gly Ala Arg Ala Ala
785                 790                 795                 800
Tyr Cys Cys Asn Gly Gly Asn Ala Ala Arg Cys Ala Arg Tyr Thr Asn
                805                 810                 815
Thr Gly Tyr Cys Ala Arg Thr Thr Tyr Trp Ser Asn Gly Cys Asn Trp
            820                 825                 830
Ser Asn Ala Cys Asn Met Gly Asn Trp Ser Asn Ala Ala Tyr Gly Thr
            835                 840                 845
Asn Gly Ala Arg Ala Cys Asn Tyr Thr Asn Tyr Thr Asn Ala Thr His
            850                 855                 860
Tyr Thr Asn Thr Thr Tyr Cys Cys Asn Tyr Thr Asn Gly Thr Asn Ala
865                 870                 875                 880
Thr His Thr Gly Tyr Tyr Thr Asn Ala Cys Asn Thr Thr Tyr Thr Ala
                885                 890                 895
Tyr Ala Cys Asn Trp Ser Asn Ala Thr Gly Ala Ala Tyr
            900                 905

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 12
acatctttgt ggtactgaat ggctcgg                                      27

<210> SEQ ID NO 13
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 13
tgagtaatgt ctcgacgttt gacctcg                                      27

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide primer
```

```
<400> SEQUENCE: 14
catcgaataa ccctgatttc ataacac                                              27

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 15
gataaagtaa gaactcgtgc c                                                    21
```